United States Patent
Weiguny et al.

(10) Patent No.: US 7,087,767 B2
(45) Date of Patent: Aug. 8, 2006

(54) METHOD FOR PRODUCING MALEIC ANHYDRIDE

(75) Inventors: Jens Weiguny, Freinsheim (DE); Wilhelm Ruppel, Mannheim (DE); Mark Duda, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/522,993

(22) PCT Filed: Jul. 22, 2003

(86) PCT No.: PCT/EP03/07982

§ 371 (c)(1),
(2), (4) Date: Feb. 2, 2005

(87) PCT Pub. No.: WO2004/014833

PCT Pub. Date: Feb. 19, 2004

(65) Prior Publication Data

US 2005/0256319 A1 Nov. 17, 2005

(30) Foreign Application Priority Data

Aug. 2, 2002 (DE) ................................ 102 35 355

(51) Int. Cl.
*C07D 307/60* (2006.01)
(52) U.S. Cl. .................. 549/259; 549/257; 549/260
(58) Field of Classification Search ................ 549/257, 549/259, 260
See application file for complete search history.

(56) References Cited

U.S. PATENT DOCUMENTS

| | | | |
|---|---|---|---|
| 3,919,257 A | 11/1975 | Milberger et al. | |
| 4,795,818 A | 1/1989 | Becker et al. | |
| 4,933,312 A | 6/1990 | Haddad et al. | |
| 5,095,125 A | 3/1992 | Haddad et al. | |
| 5,137,860 A | 8/1992 | Ebner et al. | |
| 5,158,923 A | 10/1992 | Barone | |
| 5,168,090 A | 12/1992 | Ebner et al. | |
| 5,275,996 A | 1/1994 | Andrews et al. | |
| 5,296,436 A | 3/1994 | Bortinger | |
| 5,641,722 A | 6/1997 | Mitchell et al. | |
| 2003/0065194 A1 | 4/2003 | Weiguny et al. | |

FOREIGN PATENT DOCUMENTS

| | | |
|---|---|---|
| DE | 25 39 106 A1 | 3/1977 |
| EP | 0 099 431 A1 | 2/1984 |
| EP | 0 593 646 B1 | 4/1994 |
| EP | 0 752 915 B1 | 1/1997 |
| WO | WO-93/01155 | 1/1993 |
| WO | WO-95/26817 | 12/1995 |
| WO | WO-97/12674 | 4/1997 |
| WO | WO-01/68626 A1 | 9/2001 |
| WO | WO-02/12158 A2 | 2/2002 |

OTHER PUBLICATIONS

Wellauer et al., Optimal Policies in Maleic Anhydride Production Through Detailed Reactor Modeling, Chem Eng Science, 1986, 41(4):765-772, Great Britain.
Lohbek et al., Maleic and Fumaric Acids—Maleic Anhydride (MA), 2000 Electronic Release, Ullmann's Encyclopedia of Industrial Chemistry, Sixth Ed.

*Primary Examiner*—Bernard Dentz
(74) *Attorney, Agent, or Firm*—Connolly Bove Lodge & Hutz LLP; Matthew J. Mason

(57) ABSTRACT

Process for preparing maleic anhydride by heterogeneously catalyzed gas-phase oxidation of hydrocarbons having at least four carbon atoms by means of oxygen-containing gases at from 350 to 500° C. in the presence of a volatile phosphorus compound over a vanadium-, phosphorus- and oxygen-containing catalyst in a shell-and-tube reactor unit having at least one reaction zone cooled by means of a heat transfer medium, in which the temperature and/or the amount of the heat transfer medium flowing into the first (relative to the feed direction) reaction zone are set so that the mean temperature of the heat transfer medium in the first reaction zone $T_{SB}(1^{st}\ zone)$, which is calculated as the mean of the inflow temperature and the outflow temperature of the heat transfer medium, is in accordance with the formulae (I) and (II)

Figure 1:
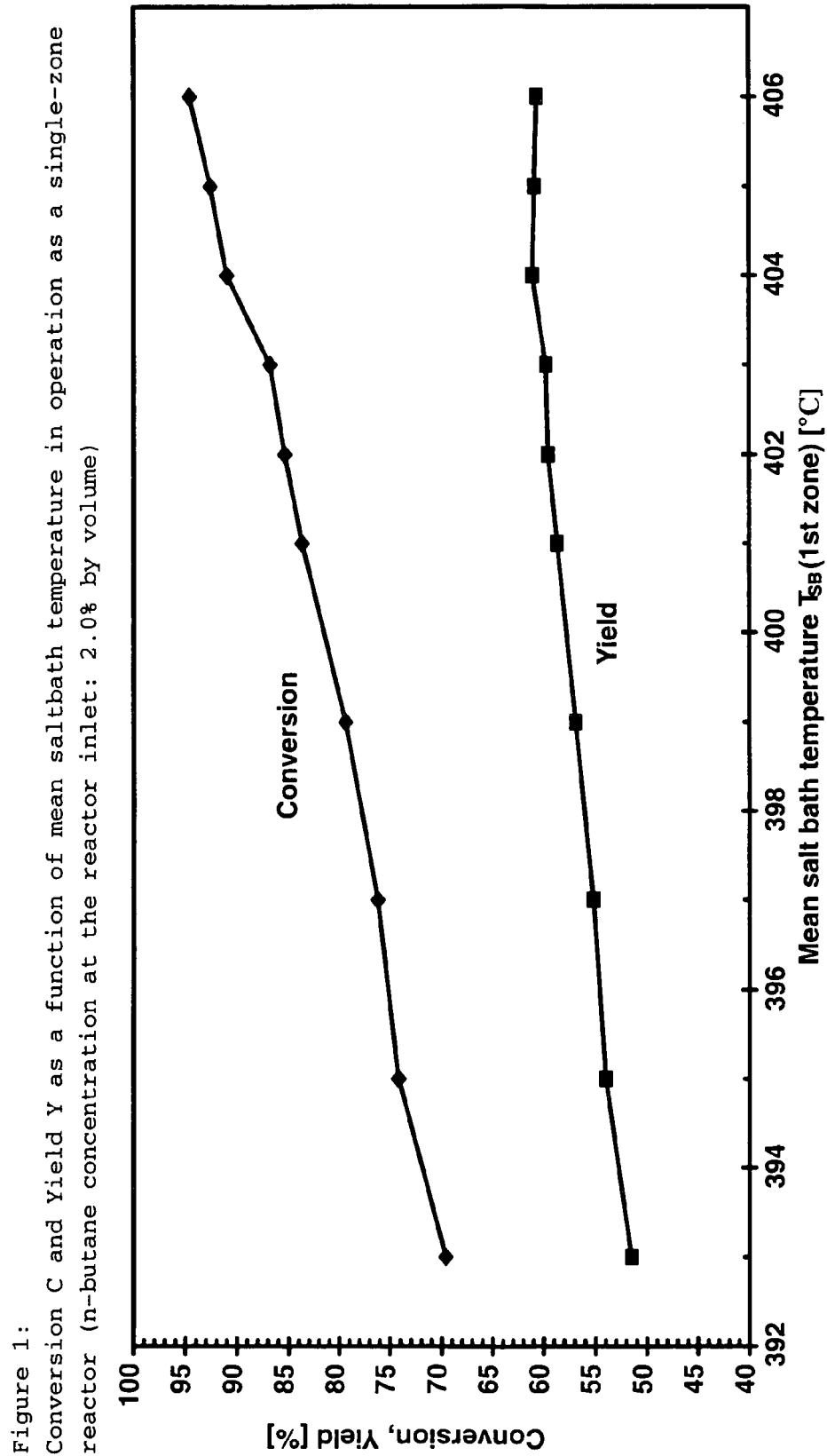

$$T_{SB}(1^{st}\ zone) \leq T_R(1^{st}\ zone) - T_{Safety}(1^{st}\ zone) \qquad (I)$$

$$T_{SB,\ Ymax}(1^{st}\ zone) - T_A(1^{st}\ zone) \leq T_{SB}(1^{st}\ zone) \leq T_{SB,\ Ymax}(1^{st}\ zone) + T_B(1^{st}\ zone), \qquad (II)$$

where
 $T_R(1^{st}\ zone)$ is the runaway temperature of the first reaction zone;
 $T_{Safety}(1^{st}\ zone)$ is the safety temperature of the first reaction zone and has a value of 1° C.;
 $T_{SB,\ Ymax}(1^{st}\ zone)$ is the mean temperature of the heat transfer medium in the first reaction zone at which the maximum maleic anhydride yield is achieved in the range $T_{SB}(1^{st}\ zone) \leq T_R(1^{st}\ zone)$;
 $T_A(1^{st}\ zone)$ is 20° C.; and
 $T_B(1^{st}\ zone)$ is 10° C.

20 Claims, 8 Drawing Sheets

Conversion C and Yield Y as a function of mean saltbath temperature in operation as a single-zone reactor (n-butane concentration at the reactor inlet: 2.0% by volume)

Hotspot temperature $T_{HS}$(1st zone) as a function of the mean saltbath temperature $T_{SB}$(1st zone) (n-butane concentration at the reactor inlet: 2.0% by volume)

Conversion C and Yield Y as a function of the mean saltbath temperature of the second zone $T_{SB}$ (2nd zone) in operation as a two-zone reactor at a mean saltbath temperature of the first zone $T_{SB}$ (1st zone) of 400°C (n-butane concentration at the reactor inlet: 2.0% by volume)

Hotspot temperature $T_{HS}$(2nd zone) as a function of the mean saltbath temperature of the second zone $T_{SB}$(2nd zone) in operation as a two-zone reactor at a mean saltbath temperature of the first zone $T_{SB}$(1st zone) of 400°C (n-butane concentration at the reactor inlet: 2.0% by volume)

Conversion C and Yield Y as a function of the mean saltbath temperature in operation as a single-zone reactor (n-butane concentration at the reactor inlet: 2.2% by volume)

Hotspot temperature $T_{HS}$(1st zone) as a function of the mean saltbath temperature $T_{SB}$(1st zone) (n-butane concentration at the reactor inlet: 2.2% by volume)

Conversion C and Yield Y as a function of the mean saltbath temperature of the second zone $T_{SB}$(2nd zone) in operation as a two-zone reactor at a mean saltbath temperature of the first zone $T_{SB}$(1st zone) of 400°C (n-butane concentration at the reactor inlet: 2.2% by volume)

Hotspot temperature $T_{HS}$(2nd zone) as a function of the mean saltbath temperature of the second zone $T_{SB}$(2nd zone) in operation as a two-zone reactor at a mean saltbath temperature of the first zone $T_{SB}$(1st zone) of 400°C (n-butane concentration at the reactor inlet: 2.2% by volume)

US 7,087,767 B2

METHOD FOR PRODUCING MALEIC ANHYDRIDE

CROSS REFERENCE TO RELATED APPLICATION

The present application is a National Stage application of PCT/EP2003/007982, filed Jul. 22, 2003, which claims priority from German Patent Application No. DE 102 35 355.7, filed Aug. 2, 2002.

The present invention relates to a process for preparing maleic anhydride by heterogeneously catalyzed gas-phase oxidation of hydrocarbons having at least four carbon atoms by means of oxygen-containing gases at from 350 to 500° C. in the presence of a volatile phosphorus compound over a vanadium-, phosphorus- and oxygen-containing catalyst in a shell-and-tube reactor unit having at least one reaction zone cooled by means of a heat transfer medium.

Maleic anhydride is an important intermediate in the synthesis of γ butyrolactone, tetrahydrofuran and 1,4-butanediol, which are in turn used as solvent or are, for example, processed further to give polymers such as polytetrahydrofuran or polyvinylpyrrolidone.

The preparation of maleic anhydride by heterogeneously catalyzed gas-phase oxidation of hydrocarbons having at least four carbon atoms by means of oxygen over a vanadium-, phosphorus- and oxygen-containing catalyst is generally known and is described, for example, in Ullmann's Encyclopedia of Industrial Chemistry, 6$^{th}$ edition, 1999 Electronic Release, Chapter "MALEIC AND FUMARIC ACID—Maleic Anhydride". In general, benzene or $C_4$-hydrocarbons such as 1,3-butadiene, n-butenes or n-butane are used as starting materials. The reaction is strongly exothermic and requires adequate removal of the heat of reaction. In general, the reaction is carried out in a shell-and-tube reactor having a circulated salt bath.

An important objective in heterogeneously catalyzed gas-phase oxidations of hydrocarbons to maleic anhydride is the achievement of a very high space-time yield of maleic anhydride over the entire life of the catalyst. The achievement of a high space-time yield of maleic anhydride is dependent on various factors, for example the type of catalyst, its activity distribution in the catalyst bed, the addition of phosphorus components to the feed mixture, the composition of the feed mixture, the space velocity of hydrocarbon over the catalyst or the reaction temperature.

Since the reaction of the hydrocarbons to form maleic anhydride proceeds strongly exothermically, a region of elevated temperature ("hotspot" region) in which the selectivity to and thus the yield of desired product is reduced as a result of many possible parallel and subsequent reactions is generally formed in the catalyst bed. To counter this effect, EP-A-0 099 431 has proposed using a structured catalyst bed, i.e. a catalyst bed of variable activity. The lowest catalyst activity is at the inlet of the reactor, and the highest is at the outlet of the reactor. In between, it can vary continuously or stepwise. To achieve the targeted setting of catalyst activities, this document teaches essentially the dilution of the active catalyst particles with inert material, the use of catalysts of different activities and, if desired, combinations thereof.

WO 93/01155 discloses a process for preparing maleic anhydride from n-butane over a vanadium-, phosphorus- and oxygen-containing catalyst in the presence of a volatile phosphorus compound, in which the catalyst activity varies with the temperature and n-butane concentration in the flow direction of the gas in such a way that the reaction rate is promoted by a high activity in a region of low temperature and low n-butane concentration within the bed and is moderated by a low activity in a critical region within the bed where the combination of temperature and n-butane concentration would lead to an excessive increase in conversion and reaction temperature.

The abovementioned structuring of the catalyst bed leads to a more uniform temperature distribution and thus generally also to an increase in the space-time yield of maleic anhydride. However, the complicated charging of the shell-and-tube reactor is a disadvantage, since the appropriate structuring has to be produced when filling each of the up to several tens of thousands of reaction tubes.

Wellauer et al., Chem. Eng. Sci. Vol. 41, No. 4 (1986), pages 765 to 772, describe a simulation model for the oxidation of n-butane to maleic anhydride on the basis of experimental data for a known catalyst. Apart from the above-described structuring of the catalyst bed, Wellauer et al. teach the setting of two different salt bath temperatures in the shell-and-tube reactor in order to increase the space-time yield. Here, a lower temperature is set in the first reaction zone nearest the feed point than in the second reaction zone at the end where the product is discharged.

WO 01/68626 teaches a process for preparing maleic anhydride from n-butane over a vanadium-, phosphorus- and oxygen-containing catalyst using a multizone shell-and-tube reactor in which the temperature difference between the hottest and coldest reaction zones is at least 2° C.

Regardless of the possible use of a structured catalyst bed or a multizone reactor, the oxidation of hydrocarbons to maleic anhydride is usually carried out at a preselected pressure and a preselected gas composition, with the salt bath temperature being set to the temperature required for a maximum yield of maleic anhydride. The salt bath temperature is generally increased continuously or in steps until the maximum maleic anhydride yield has been reached. In operation of a multizone reactor, the individual reaction zones are generally adjusted one after the other, beginning with the first reaction zone at the end nearest the feed point, to the maximum maleic anhydride yield by means of the salt bath temperature.

The present invention has recognized that the above-described adjustment of the salt bath temperature to achieve a maximum maleic anhydride yield is very critical from a safety point of view, since the resulting salt bath temperature can be in a range in which there is a risk of sudden, uncontrolled temperature peaks in the catalyst bed. These temperature peaks can lead to irreversible damage to the catalyst. There is thus a risk of damaging changes at the catalytically active catalyst surface through to sintering and caking of the catalyst. This has an adverse effect on the overall catalyst performance, in particular the activity, the selectivity and the operating life of the catalyst. Thus, for example, a salt bath temperature at which the maximum maleic anhydride yield is initially achieved can, as a result of the abovementioned possible damage to the catalyst, lead to a relatively rapid drop in the catalyst activity and selectivity and thus result in a very short operating life of the catalyst.

Furthermore, the present invention has recognized that because of the risk of sudden uncontrollable temperature peaks in the catalyst bed, it is possible in an extreme case for a "runaway" reaction to occur in individual reaction tubes or a plurality of reaction tubes through to the entire shell-and-tube reactor which may contain several tens of thousands of reaction tubes, since the reaction rate increases sharply in the region of the temperature peaks mentioned and a greater quantity of heat is thus produced at this point. In a shell-and-tube reactor, this hot region can spread via the cooling medium (salt bath) to neighboring tubes and may even spread over the entire reactor cross-section. The high temperatures, which may be up to 1000° C., can in the worst case even irreversibly damage the entire shell-and-tube reactor.

It is an object of the present invention to develop a process for preparing maleic anhydride by heterogeneously catalyzed gas-phase oxidation of a hydrocarbon having at least four carbon atoms by means of oxygen, which is unproblematical in terms of safety in respect of a runaway reaction and which also makes possible a high conversion, a high selectivity and a high yield of desired product and therefore a high space-time yield even at a high space velocity of hydrocarbon over the catalyst over a long period of time of from several months to some years and avoids or at least greatly reduces premature damage to the catalyst.

We have found that this object is achieved by a process for preparing maleic anhydride by heterogeneously catalyzed gas-phase oxidation of hydrocarbons having at least four carbon atoms by means of oxygen-containing gases at from 350 to 500° C. in the presence of a volatile phosphorus compound over a vanadium-, phosphorus- and oxygen-containing catalyst in a shell-and-tube reactor unit having at least one reaction zone cooled by means of a heat transfer medium, wherein the temperature and/or the amount of the heat transfer medium flowing into the first (relative to the feed direction) reaction zone are set so that the mean temperature of the heat transfer medium in the first reaction zone $T_{SB}(1^{st}\ zone)$, which is calculated as the mean of the inflow temperature and the outflow temperature of the heat transfer medium, is in accordance with the formulae (I) and (II)

$$T_{SB}(1^{st}\ zone) \leq T_R(1^{st}\ zone) - T_{Safety}(1^{st}\ zone) \qquad (I)$$

$$T_{SB,\ Ymax}(1^{st}\ zone) - T_A(1^{st}\ zone) \leq T_{SB}(1^{st}\ zone) \leq T_{SB,\ Ymax}(1^{st}\ zone) + T_B(1^{st}\ zone) \qquad (II),$$

where $T_R(1^{st}\ zone)$ is the runaway temperature of the first reaction zone, which corresponds to the mean temperature of the heat transfer medium $T_{SB}(1^{st}\ zone)$ at which an increase of 1° C. from a 1° C.—lower mean temperature of the heat transfer medium $T_{SB}(1^{st}\ zone) -1°\ C.$ to $T_{SB}(1^{st}\ zone)$ causes an increase of 5° C. in the hotspot temperature in the first reaction zone $T_{HS}(1^{st}\ zone)$;

$T_{Safety}(1^{st}\ zone)$ is the safety temperature of the first reaction zone and has a value of 1° C.;

$T_{SB,\ Ymax}(1^{st}\ zone)$ is the mean temperature of the heat transfer medium in the first reaction zone at which the maximum maleic anhydride yield is achieved in the range $T^{SB}(1^{st}\ zone) \leq T_R(1^{st}\ zone)$;

$T_A(1^{st}\ zone)$ is 20° C.; and $T_B(1^{st}\ zone)$ is 10° C.

In accordance with the formula (I), the process is to be operated at a mean temperature of the heat transfer medium $T_{SB}(1^{st}\ zone)$ which is lower than the previously determined runaway temperature $T_R(1^{st}\ zone)$ by at least the safety temperature $T_{Safety}(1^{st}\ zone)$ The runaway temperature $T_R(1^{st}\ zone)$ is the mean temperature of the heat transfer medium $T_{SB}(1^{st}\ zone)$ at which an increase of 1° C. from a 1° C. lower mean temperature of the heat transfer medium $T_{SB}(1^{st}\ zone) -1°\ C.$ to $T_{SB}(1^{st}\ zone)$ causes an increase of 5° C. in the hotspot temperature in the first reaction zone $T_{HS}(1^{st}\ zone)$. It has been recognized according to the present invention that the risk of a runaway reaction in one or more reaction tubes increases greatly when the hotspot temperature in the first reaction zone $T_{HS}(1^{st}\ zone)$ increases by more than 5° C.

For the purposes of the present invention, the hotspot temperature is the maximum temperature measured in the catalyst bed within the reaction zone under consideration during the chemical reaction.

The safety temperature $T_{Safety}(1^{st}\ zone)$ takes into account, in particular, the inhomogeneities present in an industrial shell-and-tube reactor unit, especially in respect of the catalyst and the density of the bed, the specific throughput in the individual tubes and the specific heat removal at the individual tubes by means of the heat transfer medium. In the process of the present invention, the safety temperature $T_{Safety}(1^{st}\ zone)$ is 1° C., preferably 2° C., particularly preferably 3° C. and very particularly preferably 4° C.

The formula (I) thus ensures that the potentially hazardous region above the runaway temperature $T_R(1^{st}\ zone)$ is not reached even in the case of the abovementioned inhomogeneities in the industrial shell-and-tube reactor units.

To achieve a high yield of maleic anhydride in addition to a safe process, the process is also to be operated in accordance with the formula (II) at a mean temperature of the heat transfer medium $T_{SB}(1^{st}\ zone)$ which is in the range from $T_{SB,\ Ymax}(1^{st}\ zone) - T_A(1^{st}\ zone)$ to $T_{SB,\ Ymax}(1^{st}\ zone) + T_B(1^{st}\ zone)$, where the temperature of maximum yield of maleic anhydride in the range $\leq T_R(1^{st}\ zone)$ is employed for $T_{SB,\ Ymax}(1^{st}\ zone)$. $T_{SB,\ Ymax}(1^{st}\ zone)$ corresponds to the mean temperature of the heat transfer medium in the first reaction zone at which the maximum yield of maleic anhydride is achieved in the range $T_{SB}(1^{st}\ zone) \leq T_R(1^{st}\ zone)$.

In the process of the present invention, the parameter $T^A(1^{st}\ zone)$ is 20° C., preferably 10° C. and particularly preferably 5° C., and the parameter $T_B(1^{st}\ zone)$ is 10° C., preferably 7° C. and particularly preferably 5° C.

The formula (II) thus ensures that a high yield of maleic anhydride is achieved in addition to a safe process.

The mean temperature of the heat transfer medium $T_{SB}(1^{st}\ zone)$ to be set in the process of the present invention thus has to be in accordance with both formula (I) and also formula (II), which is equivalent to formation of an intersection region within which $T_{SB}(1^{st}\ zone)$ is to be set.

As can be seen from the definition of $T_{SB,\ Ymax}(1^{st}\ zone)$, viz. the mean temperature of the heat transfer medium in the first reaction zone at which the maximum yield of maleic anhydride is achieved, only the region $\leq T_R(1^{st}\ zone)$ comes into consideration here. If, for example, the yield of maleic anhydride in the relevant region of $\leq T_R(1^{st}\ zone)$ increases monotonically without going through a maximum, the runaway temperature $T_R(1^{st}\ zone)$ is used as $T_{SB,\ Ymax}(1^{st}\ zone)$ in the formula (II).

If, for example, the mean temperature of the heat transfer medium in the first reaction zone $T_{SB,\ Ymax}(1^{st}\ zone)$ at which the maximum yield of maleic anhydride is obtained in the region $\leq T_R(1^{st}\ zone)$ has been determined but the runaway temperature $T_R(1^{st}\ zone)$ has not, since the latter may be at a significantly higher temperature than $T_{SB,\ Ymax}(1^{st}\ zone)$, the maximum temperature $T_{SB}(1^{st}\ zone)$ in the available data is to be used for the runaway temperature $T_R(1^{st}\ zone)$ in the formula (I) in the interest of safety. This is then reliably below the true runaway temperature $T_R(1^{st}\ zone)$.

The mean temperature of the heat transfer medium $T_{SB}(1^{st}\ zone)$ is determined by forming the mean of the inflow temperature and the outflow temperature of the heat transfer medium.

In the process of the present invention, the targeted setting of the mean temperature of the heat transfer medium $T_{SB}(1^{st}$ zone) is achieved by targeted setting of the temperature and/or amount of the heat transfer medium flowing in.

In the determination of the runaway temperature $T_R(1^{st}$ zone) and the mean temperature of the heat transfer medium $T_{SB, Ymax}(1^{st}$ zone) at which the maximum yield of maleic anhydride is achieved in the range $T_{SB}(1^{st}$ zone$)\leq T_R(1^{st}$ zone), the conditions prevailing in the process to be carried out are to be taken into account. In general, the determination is carried out experimentally in an experimental plant using the appropriate catalyst and with the parameters relevant to the reaction behavior, for example the internal diameter of the reaction tube (or reaction tubes), the pressure, the hydrocarbon concentration, the GHSV, the concentration of the volatile phosphorus compound and the concentration of any further additives such as steam being set. If the dimensions of the reactor tube used in the experimental plant are in the region of those of the reactor tubes used in the full-scale plant, a reactor tube surrounded by a heat transfer medium is generally very suitable for the determination of $T_R(1^{st}$ zone).

In the experimental determination of $T_R(1^{st}$ zone) and $T_{SB, Ymax}(1^{st}$ zone), the experimental reactor is generally operated under conditions analogous to those in the reactor to be used later. In general, a mean temperature of the heat transfer medium $T_{SB}(1^{st}$ zone) which is significantly below the expected runaway temperature $T_R(1^{st}$ zone) but gives a yield of maleic anhydride Y in the industrially relevant range is set at the end of the running-in period. Since the hotspot temperature $T_{HS}(1^{st}$ zone) is a significant parameter in the determination of the runaway temperature $T_R(1^{st}$ zone), particular attention should be paid to achieving a stable operating state. In the process of the present invention, a stable operating state is assumed when, under constant reaction conditions, the drift in the hotspot temperature $T^{HS}(1^{st}$ zone) is $\leq 0.5°$ C. over a period of 24 hours. After the hotspot temperature $T_{HS}(1^{st}$ zone) established at the set $T^{SB}(1^{st}$ zone) and the yield of maleic anhydride have been determined, the mean temperature of the heat transfer medium $T_{SB}(1^{st}$ zone) is gradually increased in steps and, in each case after a stable operating state has been established, the corresponding hotspot temperature $T_{HS}(1^{st}$ zone) and the yield of maleic anhydride are determined. If an increase of 1° C. in the mean temperature of the heat transfer medium $T_{SB}(1^{st}$ zone) causes an increase of more than 5° C. in the hotspot temperature $T_{HS}(1^{st}$ zone), the trial can generally be stopped.

In the process of the present invention, the gas-phase oxidation to maleic anhydride is carried out in a shell-and-tube reactor unit having at least one reaction zone cooled by a heat transfer medium. For the purposes of the present invention, the term shell-and-tube reactor unit refers to a unit having at least one shell-and-tube reactor. A shell-and-tube reactor in turn comprises at least one reactor tube which is surrounded by a heat transfer medium for the purpose of heating and/or cooling. In general, the shell-and-tube reactors used industrially have from a few hundred to several tens of thousands of reactor tubes connected in parallel. If a plurality of individual shell-and-tube reactors (in the sense of shell-and-tube reactor apparatuses) are connected in parallel, these are regarded as equivalent to a shell-and-tube reactor and are hereinafter encompassed by the term shell-and-tube reactor.

The shell-and-tube reactor unit can comprise one or more preheating zones which heat the inflowing gas mixture. A preheating zone integrated into a shell-and-tube reactor can be realized, for example, by means of reactor tubes which are filled with inert material and are likewise surrounded by heat transfer medium. As inert material, it is in principle possible to use all shaped bodies which are chemically inert, i.e. induce or catalyze no heterogeneously catalyzed reaction, and which have a maximum pressure drop below the respective maximum tolerable, plant-specific value. Suitable inert materials are, for example, oxidic materials such as aluminum oxide, silicon carbide or metallic materials such as stainless steel. Examples of suitable shaped bodies are spheres, pellets, hollow cylinders, rings, trilobes, tristars, wagon wheels, extrudates or irregular, crushed shaped bodies.

If the shell-and-tube reactor unit comprises a plurality of shell-and-tube reactors, for example two, three, four or more such reactors, these can be, for example, connected in parallel or connected in series. In the case of shell-and-tube reactors being connected in series, the outlet stream from one shell-and-tube reactor is passed directly into the inlet of the next shell-and-tube reactor. However, it is also possible to remove and/or introduce mass and/or energy between the two shell-and-tube reactors. Thus, for example, part of the gas stream or a component thereof can be taken off or a further gas stream can be fed in or the existing gas stream can be passed through a heat exchanger.

In the abovementioned shell-and-tube reactors, the reactor tubes are usually made of ferritic steel and typically have a wall thickness of from 1 to 3 mm. Their internal diameter is generally from 20 to 30 mm. The number of reactor tubes per shell-and-tube reactor is usually in the range from 5000 to 35000, although a number above 35000 can also be present in particularly large plants. The reactor tubes are normally distributed homogeneously within the reactor body.

The term reaction zone refers to a region within a shell-and-tube reactor, which region contains a catalyst and in which the temperature would be maintained at a uniform value by the surrounding heat transfer medium in the absence of a chemical reaction. In general, the reaction zone is delineated by the local physical dimensions of the heat transfer medium circuit. Thus, for example, a shell-and-tube reactor having only one heat transfer medium circuit also has only one reaction zone, which is by convention referred to as the first reaction zone. If a shell-and-tube reactor unit comprises, for example, a shell-and-tube reactor having two separate, successive heat transfer medium circuits, this has two reaction zones which are numbered in the flow direction of the gas.

The suitable heat transfer media are, in particular, fluid heat transfer media. It is particularly advantageous to use salt melts such as potassium nitrate, potassium nitrite, sodium nitrate and/or sodium nitrite or low-melting metals such as sodium and alloys of various metals.

In the process of the present invention, preference is given to using a shell-and-tube reactor unit having at least two reaction zones cooled by a heat transfer medium. As a result of the targeted setting of the mean temperature of the heat transfer medium $T_{SB}(1^{st}$ zone) in the first reaction zone in accordance with the formulae (I) and (II), safe operation is made possible in the zone which is particularly sensitive from a safety point of view because of the high hydrocarbon concentration which prevails. The separate reaction zones make it possible to achieve reaction conditions matched to the course of the reaction, which generally results in a higher yield of maleic anhydride and allows more flexible regulation of the process than when a single-zone reactor is used.

In the case of the preferred use of a shell-and-tube reactor unit having at least two reaction zones cooled by means of a heat transfer medium in the process of the present invention, the temperature and/or the amount of the heat transfer medium flowing into the second (relative to the feed direction) reaction zone are particularly preferably set so that the mean temperature of the heat transfer medium in the second reaction zone $T_{SB}(2^{nd}\ zone)$, which is calculated as the mean of the inflow temperature and the outflow temperature of the heat transfer medium, is in accordance with the formulae (III) and (IV)

$$T_{SB}(2^{nd}\ zone) \leq T_R(2^{nd}\ zone) - T_{Safety}(2^{nd}\ zone) \quad (III)$$

$$T_{SB,\ Ymax}(2^{nd}\ zone) - T_A(2^{nd}\ zone) \leq T_{SB}(2^{nd}\ zone)$$
$$\leq T_{SB,\ Ymax}(2^{nd}\ zone) + T_B(2^{nd}\ zone) \quad (IV),$$

where $T_R$(2nd zone) is the runaway temperature of the second reaction zone, which corresponds to the mean temperature of the heat transfer medium $T_{SB}$(2nd zone) at which an increase of 1° C. from a 1° C.—lower mean temperature of the heat transfer medium $T_{SB}(2^{nd}\ zone)-1°$ C. to $T_{SB}(2^{nd}\ zone)$ causes an increase of 5° C. in the hotspot temperature in the second reaction zone $T_{HS}(2^{nd}\ zone)$;

$T_{Safety}(2^{nd}\ zone)$ is the safety temperature of the second reaction zone and has a value of 1° C.;

$T_{SB,\ Ymax}(2^{nd}\ zone)$ is the mean temperature of the heat transfer medium in the second reaction zone at which the maximum maleic anhydride yield is achieved in the range $T^{SB}(2^{nd}\ zone) \leq T_R(2^{nd}\ zone)$;

$T_A(2^{nd}\ zone)$ is 10° C.; and $T_B(2^{nd}\ zone)$ is 10° C.

The formula (III) thus ensures that in the second reaction zone, too, the potentially hazardous region above the runaway temperature $T_R(2^{nd}\ zone)$ is not reached even when inhomogeneities occur in the industrial shell-and-tube reactor units. Furthermore, formula (IV) ensures that a high yield of maleic anhydride is achieved in addition to safe operation.

The principles described above in respect of the formulae (I) and (II) also apply to the second reaction zone. Thus, for example, the mean temperature of the heat transfer medium $T_{SB}(2^{nd}\ zone)$ is to be set so that it is in accordance with both the formula (III) and the formula (IV).

In a particularly preferred embodiment of the process of the present invention, the safety temperature $T_{Safety}(2^{nd}\ zone)$ is 1° C., preferably 2° C., particularly preferably 3° C. and very particularly preferably 4° C. The parameter $T_A$(2nd zone) is 20° C., preferably 10° C. and particularly preferably 5° C., and the parameter $T_B(2^{nd}\ zone)$ is 10° C., preferably 7° C. and particularly preferably 5° C.

In the determination of the runaway temperature $T_R(2^{nd}\ zone)$ and the mean temperature of the heat transfer medium $T_{SB,\ Ymax}(2^{nd}\ zone)$ at which the maximum yield of maleic anhydride is achieved in the region where $T_{SB}$(2nd zone) $\leq T^R(2^{nd}\ zone)$, the operating parameters in the first reaction zone have to be set beforehand to values which have previously been determined so as to meet the conditions of the formulae (I) and (II). $T_R(2^{nd}\ zone)$ and $T_{SB,\ Ymax}(2^{nd}\ zone)$ are then generally determined in a manner analogous to the above-described determination of $T_R(1^{st}\ zone)$ and $T_{SB,\ Ymax}(1^{st}\ zone)$, which is incorporated by reference at this point.

When a shell-and-tube reactor unit having at least two reaction zones cooled by means of a heat transfer medium is used, it has been found to be particularly advantageous to set the temperature and/or the amount of the heat transfer medium flowing into the second reaction zone so that the hotspot temperature in the second reaction zone $T_{HS}(2^{nd}\ zone)$ is higher than the hotspot temperature in the first reaction zone $T_{HS}(1^{st}\ zone)$. In this way, a particularly high yield of maleic anhydride is achieved.

The hotspot temperature in the second reaction zone $T^{HS}(2^{nd}\ zone)$ is preferably at least 1° C., particularly preferably at least 2° C., very particularly preferably at least 4° C. and in particular at least 6° C., higher than the hotspot temperature of the first reaction zone $T_{HS}(1^{st}\ zone)$.

Furthermore, it is advantageous to use a catalyst bed which is structured in respect of its activity in at least one of the reaction zones in the process of the present invention. This structured catalyst bed usually has a high activity in a region of low temperature and low hydrocarbon concentration and a low activity in a region in which the combination of temperature and the prevailing hydrocarbon concentration could cause an excessive rise in the reaction rate and the temperature. In general, the activity in the region of the hotspot should be reduced compared to the remainder of the catalyst bed.

The structuring of the catalyst bed can be achieved by various measures, possibly in combination. For example, it is possible to dilute the catalyst with inert material, for example shaped bodies made of steatite, aluminum oxide, silicon carbide or another inert material. It is also possible to structure the catalyst bed in respect of its activity by the use of catalysts of differing activity. This in turn can be achieved by different shaping and/or by the use of different active compositions.

The vanadium-, phosphorus- and oxygen-containing catalysts which can be used in the process of the present invention comprise, as catalytically active composition, an oxygen-containing vanadium-phosphorus compound or a mixture of such compounds. Suitable active compositions are described, for example, in the patents U.S. Pat. Nos. 5,275,996, 5,641,722, 5,137,860, 5,095,125 or 4,933,312.

They can further comprise promoters. Suitable promoters include the elements of groups 1 to 15 of the Periodic Table and their compounds. Suitable promoters are described, for example, in WO 97/12674 and WO 95/26817 and in the patents U.S. Pat. Nos. 5,137,860, 5,296,436, 5,158,923 and 4,795,818. Preferred promoters are compounds of the elements cobalt, molybdenum, iron, zinc, hafnium, zirconium, lithium, titanium, chromium, manganese, nickel, copper, boron, silicon, antimony, tin, niobium and bismuth, particularly preferably molybdenum, iron, zinc, antimony, bismuth, lithium. One or more promoters can be present in the promoter catalysts. The total promoter content of the finished catalyst is generally not more than about 5% by weight, in each case calculated as oxide.

In the production of the catalysts, it is possible to use auxiliaries such as tableting aids or pore formers.

Tableting aids are generally added if the catalysts to be used according to the present invention are shaped by means of tableting. Tableting aids are generally catalytically inert and improve the tableting properties of the precursor powder, an intermediate in catalyst production, for example by acting as a lubricant and improving powder flow. A suitable and preferred tableting aid is graphite. The tableting aids added generally remain in the activated catalyst. The content of tableting aids in the finished catalyst is typically from about 2 to 6% by weight.

Pore formers are substances which are used to set the pore structure in the macropore range in a targeted manner. They can in principle be used independently of the shaping process. They are generally compounds containing carbon, hydrogen, oxygen and/or nitrogen which are added prior to shaping of the catalyst and are mostly removed again in subsequent activation of the catalyst by sublimation, decomposition and/or vaporization. The finished catalyst can nevertheless contain residues or decomposition products of the pore former.

The catalysts which can be used in the process of the present invention can, for example, be made up of the active composition in pure, undiluted form as "all-active catalysts" or comprise the active composition diluted with a preferably oxidic support material as "mixed catalysts". Suitable support materials for mixed catalysts are, for example, aluminum oxide, silicon dioxide, aluminosilicates, zirconium dioxide, titanium dioxide or mixtures thereof. Preference is given to all-active and mixed catalysts, particularly preferably all-active catalysts.

The catalyst preferably used in the process of the present invention comprises particles having an average diameter of at least 2 mm, preferably at least 3 mm. For the present purposes, the average diameter of a particle is the mean of the smallest and largest dimension between two parallel plates.

For the purposes of the present invention, particles include both irregularly shaped particles and particles having a geometric shape, referred to as shaped bodies. The catalyst precursor to be used in the process of the present invention preferably comprises shaped bodies. Suitable shaped bodies are, for example, pellets, cylinders, hollow cylinders, spheres, rods, wagon wheels or extrudates. Special shapes such as "trilobes" and "tristars" (cf. EP-A-0 593 646) or shaped bodies having at least one notch/groove on the outside (cf. U.S. Pat. No. 5,168,090) are likewise possible.

The catalyst used in the process of the present invention particularly preferably comprises shaped bodies having an essentially hollow cylindrical structure. For the purposes of the present invention, an essentially hollow cylindrical structure is a structure which is made up essentially of a cylinder having a hole running right through between the two end faces. The cylinder is characterized by two essentially parallel end faces and a curved surface, with the cross-section of the cylinder, i.e. parallel to the end faces, being essentially circular. The cross-section of the through hole, i.e. parallel to the end faces of the cylinder, is likewise essentially circular. The through hole is preferably located centrally in the end faces, but other geometric arrangements are not ruled out.

For the present purposes, the term "essentially" indicates that deviations from the ideal geometry, for example slight deformations of the circular structure, nonparallel end faces, chipped corners and edges, surface roughness or notches/grooves in the curved surface, the end faces or the interior surface of the hole, are possible in the catalyst precursor. Within the accuracy of tableting procedures, circular end faces, a circular cross-section of the hole, parallel end faces and macroscopically smooth surfaces are preferred.

The essentially hollow cylindrical structure can be described by an external diameter $d_1$, a height h as distance between the two end faces and a diameter of the internal hole (through hole) $d_2$. The external diameter $d_1$ of the catalyst precursor is preferably from 3 to 10 mm, particularly preferably from 4 to 8 mm, very particularly preferably from 4.5 to 6 mm. The height h is preferably from 1 to 10 mm, particularly preferably from 2 to 6 mm, very particularly preferably from 2 to 4 mm. The diameter of the through hole $d_2$ is preferably from 1 to 8 mm, particularly preferably from 2 to 6 mm, very particularly preferably from 2 to 3.5 mm.

Catalyst production is generally a multistage process in which a catalyst precursor is produced first and this is subsequently converted into the active form by calcination. The catalyst precursors which can be used in the process of the present invention can be produced as described, for example, in the patents U.S. Pat. Nos. 5,275,996 and 5,641,722 or the published specification WO 97/12674. The significant steps in a preferred production of the catalyst precursor are described below.

(a) Reaction of a pentavalent vanadium compound (e.g. $V_2O_5$) and, if desired, a promoter component (e.g. $MoO_3$) with an organic reducing solvent (e.g. an alcohol such as isobutanol) in the presence of a pentavalent phosphorus compound (e.g. orthophosphoric and/or pyrophosphoric acid, phosphoric esters) and/or a trivalent phosphorus compound (e.g. phosphorous acid) with heating. This step can, if desired, be carried out in the presence of a dispersed, pulverulent support material. Preference is given to carrying out the reaction without addition of support material.

(b) Isolation of the vanadium-, phosphorus-, oxygen- and possibly promoter-containing catalyst precursor ("VPO precursor"), e.g. by filtration or evaporation.

(c) Drying of the VPO precursor and preferably incipient preactivation by heating at from 250 to 350° C. If desired, pulverulent support material and/or a pore former such as stearic acid, cellulose or paraffins can then be mixed into the dried and preferably heat-treated VPO precursor powder. Preference is given to further processing without addition of a support material and without addition of a pore former.

(d) Shaping to achieve conversion into the desired structure, preferably into the essentially hollow cylindrical structure. Shaping is preferably carried out by tableting, advantageously with prior mixing-in of a lubricant such as graphite.

A less preferred alternative to tableting is, for example, extrusion. In this variant, the VPO precursor obtained in (b) is, for example, mixed with liquid to give an extrudable mass. This can then be extruded to form the desired structure and dried to give the catalyst precursor.

The calcination of the catalyst precursor is generally carried out in the presence of an atmosphere comprising oxygen, hydrogen oxide (water vapor) and/or inert gas in a temperature range from 250 to 600° C. The suitable inert gases are, for example, nitrogen, carbon dioxide and noble gases. In the calcination to produce the catalyst to be used in the process of the present invention, the catalyst precursor preferably goes through at least two calcination zones, for example from two to ten calcination zones, each having a different gas atmosphere and possibly a different temperature. A suitable combination of temperatures, treatment times and gas atmospheres matched to the respective catalyst system enables the mechanical and catalytic properties of the catalyst to be influenced and thus to be set in a targeted manner.

Preference is given to a calcination in which the catalyst precursor is (a) in at least one calcination zone, heated to a temperature of from 200 to 350° C. in an oxidizing atmosphere having an oxygen content of from 2 to 21% by volume and kept under these conditions until the desired average oxidation state of the vanadium has been achieved; and (b) in at least one further calcination zone, heated to a temperature of from 300 to 500° C. in a nonoxidizing atmosphere having an oxygen content of $\leqq 0.5\%$ by volume and a hydrogen oxide content of from 20 to 75% by volume and kept under these conditions for $\geqq 0.5$ hours.

In step (a), the catalyst precursor is kept in an oxidizing atmosphere having a content of molecular oxygen of generally from 2 to 21% by volume, preferably from 5 to 21% by volume, at a temperature of from 200 to 350° C., preferably from 250 to 350° C., for a period which results in the desired average oxidation state of the vanadium. In general, mixtures of oxygen, inert gases (e.g. nitrogen or argon), hydrogen oxide (water vapor) and/or air or air itself are used in step (a). The temperature experienced by the catalyst precursor being passed through the calcination zone(s) during the calcination step (a) can be kept constant or can, on average, rise or fall. Since the step (a) is generally preceded by a heating phase, the temperature will in general firstly rise and then oscillate and settle down to the desired final value. The calcination zone of step (a) is therefore generally preceded by at least one further calcination zone for heating up the catalyst precursor.

The period for which the heat treatment in step (a) is maintained is, for the purposes of the present invention, preferably selected so that an average oxidation state of the vanadium in the range from +3.9 to +4.4, preferably from +4.0 to +4.3, is obtained. The average oxidation state of the vanadium is determined by potentiometric titration using the method described in the examples.

Since the determination of the average oxidation state of the vanadium during the calcination is extremely difficult for equipment and time reasons, the time required is advantageously determined experimentally in preliminary tests. In general, this is carried out by means of a series of measurements in which samples of the catalyst precursor are heat treated under defined conditions and the samples are removed from the system after different times, cooled and analyzed to determine the average oxidation state of the vanadium.

The period of time required in step (a) is generally dependent on the nature of the catalyst precursor, the temperature set and the gas atmosphere selected, in particular its oxygen content. In general, the period of time in step (a) extends up to a time of more than 0.5 hours, preferably more than 1 hour. In general, a period of up to 4 hours, preferably up to 2 hours, is sufficient to achieve the desired average oxidation state. However, under appropriate conditions (e.g. bottom part of the temperature range and/or low content of molecular oxygen), a period of more than 6 hours may also be necessary.

In step (b), the catalyst intermediate obtained is kept in a nonoxidizing atmosphere having a content of molecular oxygen of $\leqq 0.5\%$ by volume and of hydrogen oxide (water vapor) of from 20 to 75% by volume, preferably from 30 to 60% by volume, at a temperature of from 300 to 500° C., preferably from 350 to 450° C., for a period of $\geqq 0.5$ hours, preferably from 2 to 10 hours and particularly preferably from 2 to 4 hours. In general, the nonoxidizing atmosphere comprises the abovementioned hydrogen oxide together with predominantly nitrogen and/or noble gases such as argon, but this does not constitute a restriction. Gases comprising, for example, carbon dioxide are also suitable in principle. The nonoxidizing atmosphere preferably contains $\geqq 40\%$ by weight of nitrogen. The temperature experienced by the catalyst precursor passed through the calcination zone(s) during the calcination step (b) can be kept constant or can, on average, rise or fall. If step (b) is carried out at a temperature which is higher or lower than in step (a), a heating or cooling phase is generally present between the steps (a) and (b). This heating or cooling phase may be implemented in a further calcination zone. To improve separation from the oxygen-containing atmosphere of step (a), this further calcination zone between (a) and (b) can, for example, be flushed with inert gas, for example nitrogen. Step (b) is preferably carried out at a temperature which is from 50 to 150° C. higher than that in step (a).

The calcination generally comprises a further step (c) to be carried out at a later time than step (b). In this step (c), the calcined catalyst precursor is cooled to $\leqq 300°$ C., preferably $\leqq 200°$ C. and particularly preferably $\leqq 150°$ C., in an inert gas atmosphere.

Further steps are possible before, between and/or after the steps (a) and (b) or (a), (b) and (c) in the calcination carried out for the purposes of the present invention. Without implying a restriction, further steps may be, for example, changes in the temperature (heating, cooling), changes in the gas atmosphere (change to a different gas atmosphere), further hold times, transfer of the catalyst intermediate to other apparatuses or interruption of the entire calcination procedure.

Since the catalyst precursor is generally at <100° C. before commencement of calcination, it usually has to be heated up before step (a). Heating up can be carried out using various gas atmospheres. Heating up is preferably carried out in an oxidizing atmosphere as defined under step (a) or in an inert gas atmosphere as defined under step (c). A change of gas atmosphere during the heating phase is also possible. Particular preference is given to heating up the catalyst precursor in the same oxidizing atmosphere that is employed in step (a).

The catalysts which are preferably used in the process of the present invention have an atomic ratio of phosphorus to vanadium of from 0.9 to 1.5, particularly preferably from 0.9 to 1.2 and very particularly preferably from 1.0 to 1.1, an average oxidation state of the vanadium of from +3.9 to +4.4, particularly preferably from 4.0 to 4.3, a BET surface area of from 10 to 50 $m^2/g$, particularly preferably from 20 to 40 $m^2/g$, a pore volume of from 0.1 to 0.5 ml/g, particularly preferably from 0.2 to 0.4 ml/g, and a bulk density of from 0.5 to 1.5 kg/l, particularly preferably from 0.5 to 1.0 kg/l.

As hydrocarbons having at least four carbon atoms, it is possible to use aliphatic and aromatic, saturated and unsaturated hydrocarbons having at least four carbon atoms, for example 1,3-butadiene, 1-butene, cis-2-butene, trans-2-butene, n-butane, a $C_4$ mixture, 1,3-pentadiene, 1,4-pentadiene, 1-pentene, cis-2-pentene, trans-2-pentene, n-pentane, cyclopentadiene, dicyclopentadiene, cyclopentene, cyclopentane, a $C_5$ mixture, hexenes, hexanes, cyclohexane and benzene, in the process of the present invention. Preference is given to using 1-butene, cis-2-butene, trans-2-butene, n-butane, benzene or mixtures thereof. Particular preference is given to using n-butane and n-butane-containing gases and liquids. The n-butane used preferably originates from natural gas, from steam crackers or from FCC plants.

The hydrocarbon is generally introduced at a regulated rate, i.e. with maintenance of a defined quantity per unit time. The hydrocarbon can be metered in in liquid or gaseous form. It is preferably metered in in liquid form with subsequent vaporization before it enters the shell-and-tube reactor.

As oxidant, use is made of oxygen-containing gases such as air, synthetic air, a gas enriched with oxygen or "pure"

oxygen, i.e. the oxygen from, for example, fractionation of air. The oxygen-containing gas is also introduced at a regulated rate.

The gas to be passed through the shell-and-tube reactor generally has a hydrocarbon concentration of from 0.5 to 15% by volume and an oxygen concentration of from 8 to 25% by volume. The balance to 100% by volume is made up of further gases such as nitrogen, noble gases, carbon monoxide, carbon dioxide, water vapor, oxygenated hydrocarbons (e.g. methanol, formaldehyde, formic acid, ethanol, acetaldehyde, acetic acid, propanol, propionaldehyde, propionic acid, acrolein, crotonaldehyde) and mixtures thereof. The proportion of n-butane, based on the total amount of hydrocarbons, is preferably ≧90% and particularly preferably ≧95%.

To ensure a long operating life of the catalyst and to achieve a further increase in conversion, selectivity, yield, space velocity over the catalyst and space-time yield, preference is given to adding a volatile phosphorus compound to the gas in the process of the present invention. Its concentration in the feed at the inlet to the reactor is at least 0.2 ppm by volume, i.e. $0.2 \times 10^{-6}$ parts by volume of the volatile phosphorus compound per one part by volume of the total gas at the reactor inlet. Preference is given to a content of from 0.2 to 20 ppm by volume, particularly preferably from 0.5 to 10 ppm by volume. For the purposes of the present invention, volatile phosphorus compounds are all phosphorus-containing compounds which are present in gaseous form in the desired concentration under the conditions of use. Examples of suitable volatile phosphorus compounds are phosphines and phosphoric esters. Particular preference is given to tri($C_1$–$C_4$-alkyl) phosphates, very particularly preferably trimethyl phosphate, triethyl phosphate and tripropyl phosphate, in particular triethyl phosphate.

The process of the present invention is carried out at from 350 to 500° C. For the purposes of the present invention, this temperature is the mean temperature of the heat transfer medium. The process of the present invention is preferably carried out at from 380 to 460° C. and particularly preferably at from 380 to 440° C.

The process of the present invention can be carried out at subatmospheric pressure (e.g. down to 0.05 MPa abs) or at superatmospheric pressure (e.g. up to 10 MPa abs). For the purposes of the present invention, this pressure is the pressure in the shell-and-tube reactor unit at the reactor outlet. Preference is given to a pressure of from 0.075 to 1.0 MPa abs, particularly preferably from 0.075 to 0.5 MPa abs.

The process of the present invention can be carried out in two preferred process variants, namely the "single pass" variant and the variant with "recirculation". In the "single pass" variant, maleic anhydride and; if appropriate, oxygenated hydrocarbon by-products are separated off from the output from the reactor and the remaining gas mixture is discharged and, if appropriate, utilized thermally. In the "recirculation" variant, maleic anhydride and, if appropriate, oxygenated hydrocarbon by-products are likewise separated off from the output from the reactor, but the remaining gas mixture, which comprises unreacted hydrocarbon, is wholly or partly recirculated to the reactor. A further variant of the "recirculation" procedure comprises separating off the unreacted hydrocarbon and recirculating it to the reactor.

In a particularly preferred embodiment of the process for preparing maleic anhydride, n-butane is used as starting hydrocarbon and the heterogeneously catalyzed gas-phase oxidation is carried out in a "single pass" in the presence of air as oxygen-containing gas and of triethyl phosphate as volatile phosphorus compound in a shell-and-tube reactor unit having two reaction zones which are each cooled by means of a salt melt circuit. The first reaction zone is operated in a region determined according to the formulae (I) and (II) and the second reaction zone is operated under conditions determined according to the formulae (III) and (IV). The values of $T_R(1^{st}$ zone), $T_{SB, Ymax}(1^{st}$ zone), $T_R(2^{nd}$ zone) and $T_{SB, Ymax}(2^{nd}$ zone) are determined experimentally in tests carried out beforehand in a suitable experimental plant.

The process of the present invention for preparing maleic anhydride makes safe reactor operation without the risk of a runaway reaction possible and leads to a high conversion, a high selectivity and a high yield of desired product even at a high space velocity of hydrocarbon over the catalyst over a prolonged period of from several months to a number of years. In this way, a high space-time yield is achieved while premature damage to the catalyst is avoided or at least greatly reduced.

Definitions

The parameters referred to in this text are, unless indicated otherwise, defined as follows:

$$\text{Space-time yield} = \frac{m_{maleic\ anhydride}}{V_{catalyst} \cdot t}$$

$$\text{Hydrocarbon space velocity} = \frac{V_{hydrocarbon}}{V_{catalyst} \cdot t}$$

$$GHSV(\text{gas hourly space velocity}) = \frac{V_{gas}}{V_{catalyst} \cdot t}$$

$$\text{Conversion } C = \frac{n_{HC,reactor\ in} - n_{HC,reactor,out}}{n_{HC,reactor,in}}$$

$$\text{Selectivity } S = \frac{n_{MA,reactor,out}}{n_{HC,reactor,in} - n_{HC,reactor,out}}$$

$$\text{Yield } Y = C \cdot S$$

| | |
|---|---|
| $m_{maleic\ anhydride}$ | mass of maleic anhydride produced [g] |
| $V_{catalyst}$ | bed volume of catalyst, total over all reaction zones [l] |
| $t$ | time [h] |
| $V_{hydrocarbon}$ | volume at 0° C. and 0.1013 MPa of the hydrocarbon in the gas phase at the reactor inlet [standard l] (mathematical parameter, if a hydrocarbon is liquid under these conditions, the hypothetical gas volume is calculated by means of the ideal gas law.) |
| $V_{Gas}$ | volume at 0° C. and 0.1013 MPa of the total amount of gas at the reactor inlet [standard l] |
| C | conversion of hydrocarbons per pass through the reactor |
| S | Selectivity to maleic anhydride per pass through the reactor |
| Y | Yield of maleic anhydride per pass through the reactor |
| $n_{HC,\ reactor,\ in}$ | molar flow of hydrocarbons at the reactor inlet [mol/h] |
| $n_{HC,\ reactor,\ out}$ | molar flow of hydrocarbons at the reactor outlet [mol/h] |
| $n_{MA,\ reactor,\ out}$ | molar flow of maleic anhydride at the reactor outlet [mol/h] |
| $T_{SB}(1^{st}$ zone): | Mean salt bath temperature in, the first reaction zone |
| $T_{HS}(1^{st}$ zone): | Hotspot temperature in the first reaction zone |
| $T_{SB}(2^{nd}$ zone): | Mean salt bath temperature in the second reaction zone |
| $T_{HS}(2^{nd}$ zone): | Hotspot temperature in the second reaction zone |

EXAMPLES

Determination of the Average Oxidation State of the Vanadium

The average oxidation state of the vanadium was determined by potentiometric titration.

For the determination, 200–300 mg of the sample are in each case added under an argon atmosphere to a mixture of 15 ml of 50% strength sulfuric acid and 5 ml of 85% strength phosphoric acid and are dissolved with heating. The solution is subsequently transferred to a titration vessel equipped with two Pt electrodes. The titrations are in each case carried out at 80° C. The solution is firstly titrated with 0.1 molar potassium permanganate solution. If two steps are obtained in the potentiometric curve, the vanadium was present in an average oxidation state of from +3 to <+4. If only one step is obtained, the vanadium was present in an oxidation state of from +4 to <+5.

In the first case (two steps/+3≦$V_{ox}$<+4) the solution contains no $V^{5+}$, i.e. all the vanadium has been measured titrimetrically. The amounts of $V^{3+}$ and $V^{4+}$ are calculated from the consumption of the 0.1 molar potassium permanganate solution and the position of the two steps. The weighted average then gives the average oxidation state.

In the second case (one step/+4≦$V_{ox}$<+5), the amount of $V^{4+}$ can be calculated from the consumption of the 0.1 molar potassium permanganate solution. Subsequent reduction of all the $V^{5+}$ in the resulting solution by means of a 0.1 molar ammonium iron(II) sulfate solution and reoxidation using 0.1 molar potassium permanganate solution enables the total amount of vanadium to be calculated. The difference between the total amount of vanadium and the amount of $V^{4+}$ gives the amount of $V^{5+}$ originally present. The weighted average then gives the average oxidation state.

Determination of the Lateral Compressive Strength of the Hollow Cylinders

To determine the lateral compressive strength, the hollow cylinders were, in successive measurements, in each case placed lying on their curved sides on the flat metal bottom plate of an appropriate measuring apparatus. The two parallel end faces were thus vertical. A flat metal upper plate was then moved downward onto the hollow cylinder at an advance rate of 1.6 mm/min and the force on the hollow cylinder until fracture occurred was recorded as a fraction of time. The lateral compressive strength of the individual hollow cylinder corresponds to the maximum force applied.

To determine the lateral compressive strength, 30 individual measurements were carried out in each case and the mean was calculated.

Determination of Abrasion

To determine the abrasion, about 50 g of dedusted hollow cylinders were placed in a Plexiglas drum having an internal diameter of 290 mm, a drum height of 40 mm and a Plexiglas insert which has a circular curvature (radius 80 mm), extends over the entire drum height of 40 mm, is located between the axis of rotation and the outer wall and is fixed to the Plexiglas drum. The Plexiglas drum, whose axis of rotation was horizontal, was then rotated at 25 revolutions per minute for 18 minutes. The material abraded from the sample was then sieved out, the remaining particles were dedusted and reweighed. The abrasion value is then given by the loss in mass divided by the original mass.

Experimental Plant

The experimental plant was equipped with a feed unit and a reactor tube. Replacement of a shell-and-tube reactor by a single reactor tube is readily possible on a laboratory or pilot plant scale as long as the dimensions of the reactor tube are in the region of those of an industrial reactor tube. The plant was operated in a "single pass".

The hydrocarbon was introduced in liquid form at a regulated rate by means of a pump. As oxygen-containing gas, air was added at a regulated rate. Triethyl phosphate (TEP) was likewise added in liquid form, as a solution in water, at a regulated rate.

The shell-and-tube reactor unit consisted of a shell-and-tube reactor having a single reactor tube. The length of the reactor tube was 6.5 m and the internal diameter was 22.3 mm. A multithermocouple having 20 temperature measurement points and located in a protective sheath having an external diameter of 6 mm was installed inside the reactor tube. The temperature of the reactor was controlled by means of two heat transfer medium circuits which were located one after the other and each had a length of 3.25 m and could be regulated separately. The heat transfer medium used was a salt melt.

The reaction gas mixture flowed from the top downward through the reactor tube. The upper 0.2 m of the 6.5 m long reactor tube remained unfilled. Next there was a 0.3 m long preheating zone which was filled with shaped steatite bodies as inert material. The preheating zone was followed by the catalyst bed containing a total of 2144 ml of catalyst.

Immediately downstream of the shell-and-tube reactor unit, gaseous product was taken off and passed to the on-line gas chromatograph. The main stream of the gaseous reactor output was discharged from the plant.

Production of the Catalyst 6.1 $m^3$ of isobutanol were placed in an 8 $m^3$-enamelled steel stirred vessel which was provided with baffles, could be heated externally by means of pressure water and had been made inert with nitrogen. After starting up the three-stage impeller stirrer, the isobutanol was heated to 90° C. under reflux. At this temperature, the addition of 736 kg of vanadium pentoxide via the feed screw was then commenced. After about ⅔ of the desired amount of vanadium pentoxide had been added after about 20 minutes, the pumping-in of 900 kg of 105% strength phosphoric acid was commenced while continuing to add vanadium pentoxide. To clean the pump, a further 0.2 $m^3$ of isobutanol were pumped in afterwards. The reaction mixture was subsequently heated to about 100–108° C. under reflux and kept under these conditions for 14 hours. The hot suspension was subsequently drained into a pressure filter which had previously been heated and made inert with nitrogen and was filtered at about 100° C. and a pressure above the filter of up to 0.35 MPa abs. The filter cake was blown dry by passing nitrogen through it continually at 100° C. for a period of about one hour while stirring with a centrally located stirrer whose height could be adjusted. After the filter cake had been blown dry, it was heated to about 155° C. and the filter was evacuated to a pressure of 15 kPa abs (150 mbar abs). Drying was carried out to a residual isobutanol content of <2% by weight in the dried catalyst precursor.

The dried powder was subsequently treated under air in a rotating tube having a length of 6.5 m and an internal diameter of 0.9 m and provided with helical internals for 2 hours. The rate of rotation of the rotating tube was 0.4 rpm. The powder was fed into the rotating tube at a rate of 60 kg/h. The air was introduced at a rate of 100 m³/h. The temperatures measured directly on the outside of the rotating tube in the five equal-length heating zones were 250° C., 300° C., 340° C., 340° C. and 340° C. After cooling to room temperature, the VPO precursor was intimately mixed with 1% by weight of graphite and compacted in a roller compactor. The fines having a particle size of <400 µm in the compacted material were sieved out and returned to the compaction process. The coarse material having a particle size of ≧400 µm was mixed with a further 2% by weight of graphite and tabulated in a tableting machine to form 5×3×2.5 mm hollow cylinders (external diameter× height× diameter of the internal hole) having a lateral compressive strength of 11 N. To obtain the required amount of catalyst precursor, a number of batches were processed.

About 2.7 metric tons of the 5×3×2.5 mm hollow cylinders obtained were introduced continuously in a bed height of 9–10 cm on a gas-permeable conveyor belt into a belt calcination apparatus comprising two identical belt calcination units which were connected in series and had a total of eight calcination zones. The first 1.4 metric tons were used for setting the operating parameters of the belt calcination apparatus. Since they do not represent uniform material, they were disregarded in the following.

The belt calcination apparatus was operated at atmospheric pressure. An encapsulated transition zone was located between the calcination zones 4 and 5. Each of the eight calcination zones was provided with a fan to generate gas circulation. Each of the eight calcination zones was supplied with the desired amount of desired fresh gas. To maintain the desired pressure of the atmosphere, an appropriate amount of gas was discharged. The volume of gas circulating in each calcination zone per unit time was greater than the volume of the gas introduced or discharged per unit time. A dividing wall open in the region of the stream of catalyst precursor was located between each of the successive calcination zones to reduce gas exchange. The length of each calcination zone was 1.45 m. The speed of the conveyor belt was set to give the desired residence time of about 2 hours per calcination zone. The individual zones were operated as shown in Table 1:

TABLE 1

Parameters for operation of the belt calcination apparatus.

| Zone | Temperature | Fresh gas fed in |
|---|---|---|
| Calcination zone 1 | Heating to 250° C. | Air |
| Calcination zone 2 | Hold at 250° C. | Air |
| Calcination zone 3 | Hold at 250° C. | Air |
| Calcination zone 4 | Heating to 310° C. | Air |
| Transition zone | Cooling to 200° C. | Air |
| Calcination zone 5 | Heating to 425° C. | $N_2$ |
| Calcination zone 6 | Hold at 425° C. | $N_2/H_2O$ vapor (1:1) |
| Calcination zone 7 | Hold at 425° C. | $N_2/H_2O$ vapor (1:1) |
| Calcination zone 8 | Cooling to room temperature | $N_2$ |

In this way, about 1.3 metric tons of finished catalyst were produced continuously. A representative sample of this catalyst had the following properties:

| | |
|---|---|
| average oxidation state of the vanadium ($V_{ox}$): | 4.16 |
| lateral compressive strength (LCS): | 10.1 N |
| abrasion: | 0.7% by weight. |

Example 1

Single-zone Reactor (2.0% by Volume of N-butane)

In the case of the single-zone reactor, both heat transfer medium circuits were operated at the same salt bath temperature. The reaction conditions set were as follows:

| | |
|---|---|
| Total amount of catalyst installed: | 2144 ml |
| Concentration of n-butane at the reactor inlet: | 2.0% by volume |
| GHSV: | 2000 standard $l/l_{catalyst} \cdot h$ |
| Concentration of triethyl phosphate (TEP) at the reactor inlet: | 2 ppm by volume |
| Concentration of water vapor at the reactor inlet: | 3% by volume |

Example 1A

Determination of the Runaway Temperature $T_R(1^{st}$ Zone)

The catalyst was started up at a mean salt bath temperature $T_{SB}$ of 360° C., a concentration of n-butane at the reactor inlet of 1.0% by volume, a GHSV of 1700 standard $l/l_{catalyst} \cdot h$ and a concentration of water vapor at the reactor inlet of 3% by volume. Over a period of 7 days, the concentration of n-butane at the reactor inlet was gradually increased to 2.0% by volume, the GHSV was increased to 2000 standard $l/l_{catalyst} \cdot h$ and the mean salt bath temperature $T_{SB}$ was increased to 393° C. and the establishment of a stable operating state, i.e. a state at which the drift in the hotspot temperature $T_{HS}(1^{st}$ zone) over 24 hours was ≦0.5° C., under these conditions was awaited. The mean salt bath temperature was then increased in steps, firstly in steps of 2° C. and then, above 401° C., in steps of 1° C. After a stable operating state had been reached, the hotspot temperature $T^{HS}(1^{st}$ zone), the conversion C, the yield Y and the selectivity S were determined. At the salt bath temperatures set, all hotspots were in the region of the upper heat transfer medium circuit.

FIG. 1 shows the conversion C and yield Y as a function of the mean salt bath temperature. With increasing mean salt bath temperature, the conversion C rises continuously in the range examined, while the yield of maleic anhydride displays a maximum of 61.1% at a mean salt bath temperature $T_{SB, Ymax}(1^{st}$ zone) of 404° C.

Figure 2:
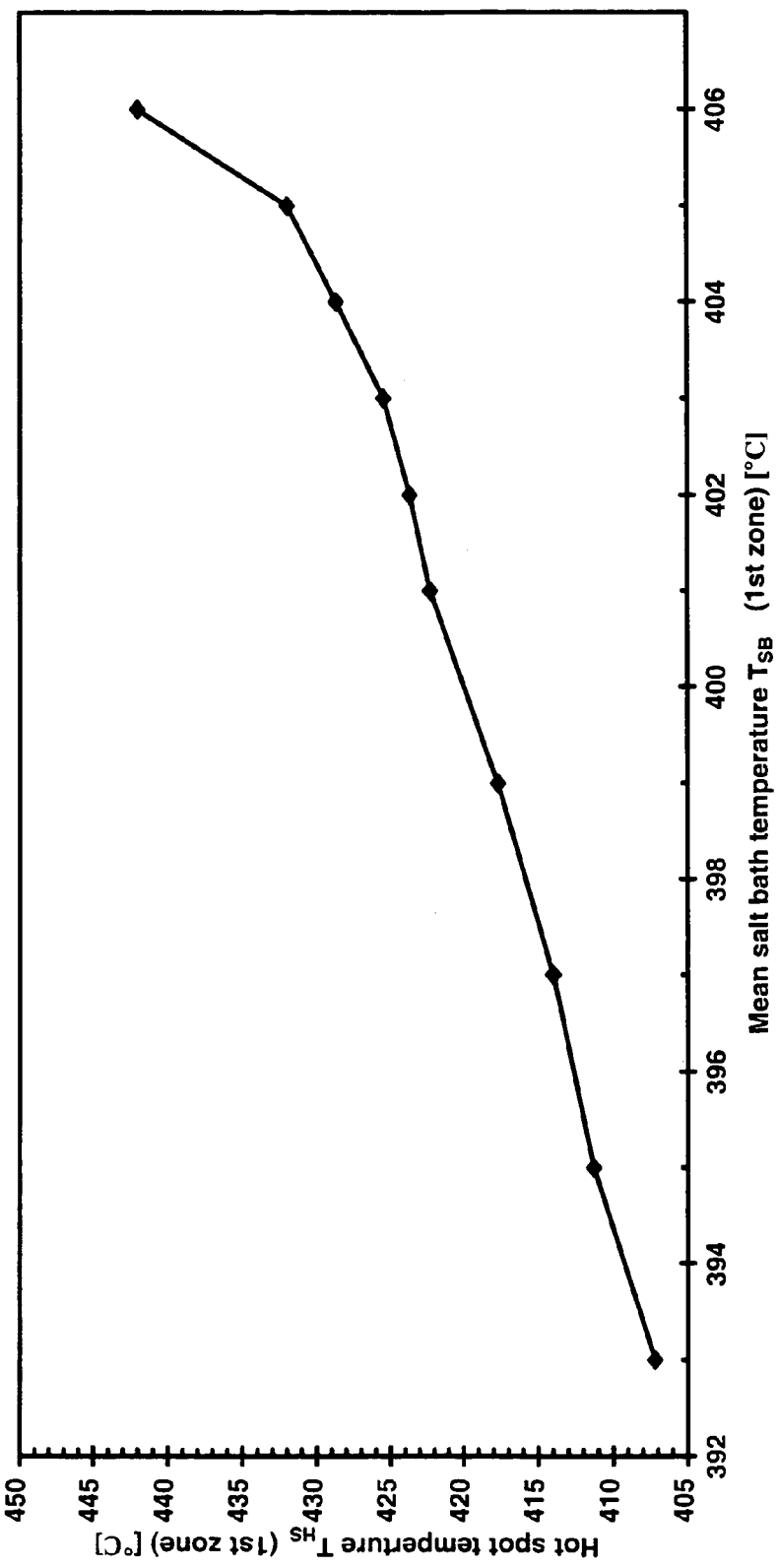

FIG. 2 shows the hotspot temperature $T_{HS}(1^{st}$ zone) as a function of the mean salt bath temperature $T_{SB}(1^{st}$ zone). An increase of 1° C. in the mean salt bath temperature $T_{SB}(1^{st}$ zone) from 404° C. to 405° C. leads to an increase of 3.3° C. in the hotspot temperature $T_{HS}(1^{st}$ zone). A further increase of 1° C. in the mean salt bath temperature $T_{SB}(1^{st}$ zone) to 406° C. leads to an increase of 10.0° C. in the hotspot temperature $T_{HS}(1^{st}$ zone). The runaway temperature $T_R(1^{st}$ zone) is thus between 405 and 406° C. An approximate valuation based on linear interpolation between the measured values gives a runaway temperature $T_R(1^{st}$ zone) of about 405.3° C.

Example 1B

Selection of the Operating Range of the Single-zone Reactor

Based on the experimentally determined runaway temperature $T_R(1^{st}$ zone) of 405.3° C., formula (I) gives a range for the mean salt bath temperature $T_{SB}(1^{st}$ zone) to be set of $$T_{SB}(1^{st}\text{ zone}) \leq 405.3° \text{ C.} - 1° \text{ C.}$$

and on the basis of the experimentally determined mean salt bath temperature $T_{SB, Ymax}(1^{st}$ zone) at which the maximum yield of maleic anhydride is achieved in the range $T_{SB}(1^{st}$ zone)$\leq 405.3°$ C. of 404° C., formula (II) gives a range for the mean salt bath temperature $T_{SB}(1^{st}$ zone) to be set of $$404° \text{ C.} - 20° \text{ C.} \leq T_{SB}(1^{st}\text{ zone}) \leq 404° \text{ C.} + 10° \text{ C.}$$

The mean salt bath temperature $T_{SB}(1^{st}$ zone) for operation of the single-zone reactor in accordance with the present invention when using the chosen catalyst and under the operating conditions selected is thus in the range from 384 to 404.3° C. However, to obtain the highest possible yield of maleic anhydride and to achieve a very high level of safety, it is particularly advantageous to carry out the process at a mean salt bath temperature $T_{SB}(1^{st}$ zone) in the range from (404−5)° C. to (405.3−2)° C., i.e. in the range from 399 to 403.3° C., which corresponds to a yield of maleic anhydride of from about 56.9 to 59.8%. In particular, to achieve a particularly high level of safety, it is highly advantageous to carry out the process at a mean salt bath temperature $T_{SB}(1^{st}$ zone) in the range from (404−5)° C. to (405.3−4)° C., i.e. in the range from 399 to 401.3° C., which corresponds to a yield of maleic anhydride of from about 56.9 to 58.7%.

It should be emphasized that the experimentally determined maximum maleic anhydride yield of 61.1% is obtained at a mean salt bath temperature $T_{SB}(1^{st}$ zone) of 404° C. In the present case, the mean salt bath temperature $T_{SB}(1^{st}$ zone) to be set is limited according to the formula (I) to $\leq 404.30°$ C., preferably 403.3° C. and particularly preferably 401.3° C., and the danger of sudden, uncontrolled temperature peaks in the catalyst bed of the shell-and-tube reactor, which could irreversibly damage the catalyst, is thereby significantly reduced or ruled out. The measures provided by the present invention thus rule out this hazardous region and ensure safe operation of the process and avoid premature thermal damage to the catalyst.

Example 2

Two-zone Reactor (2.0% by Volume of N-butane)

The reaction conditions set were as follows:

| | |
|---|---|
| Total amount of catalyst installed: | 2144 ml |
| Concentration of n-butane at the reactor inlet: | 2.0% by volume |
| GHSV: | 2000 standard $l/l_{catalyst} \cdot h$ |
| Concentration of triethyl phosphate (TEP) at the reactor inlet: | 2 ppm by volume |
| Concentration of water vapor at the reactor inlet: | 3% by volume |

Since the reaction conditions in the upper reaction zone of the single-zone reactor and the first reaction zone of the two-zone reactor are identical, the runaway temperature $T^R(1^{st}$ zone) of the single-zone reactor is also identical to the runaway temperature of the first reaction zone $T_R(1^{st}$ zone) of the two-zone reactor. The determination of the runaway temperature of the first reaction zone $T_R(1^{st}$ zone) of the two-zone reactor and the selection of the appropriate operating range as in Example 1.

The first reaction zone of the two-zone reactor is thus to be operated at a mean salt bath temperature $T_{SB}(1^{st}$ zone) in the range from 384 to 404.3° C., particularly advantageously in the range from 399 to 403.3° C. and very particularly advantageously in the range from 399 to 401.3° C., when using the chosen catalyst and under the operating conditions selected.

Example 2A

Determination of the Runaway Temperature $T_R(2^{nd}$ Zone)

In the present example, the first reaction zone of the two-zone reactor was operated at a mean salt bath temperature $T_{SB}(1^{st}$ zone) of 400° C.

The catalyst was operated initially at a mean salt bath temperature of the first reaction zone $T_{SB}(1^{st}$ zone) of 400° C. and a mean salt bath temperature of the second reaction zone $T_{SB}(2^{nd}$ zone) of 402° C. until a stable operating state had been established. The mean salt bath temperature of the second reaction zone $T_{SB}(2\text{nd zone})$ was then increased in steps of 1° C. and the establishment of a stable operating state, i.e. a state in which the drift of the hotspot temperature $T_{HS}(2^{nd}$ zone) was $\leq 0.5°$ C. over a period of 24 hours, was awaited each time. After a stable operating state had been reached, the hotspot temperature $T_{HS}(2^{nd}$ zone), the conversion C, the yield Y and the selectivity S were determined in each case.

Figure 3:
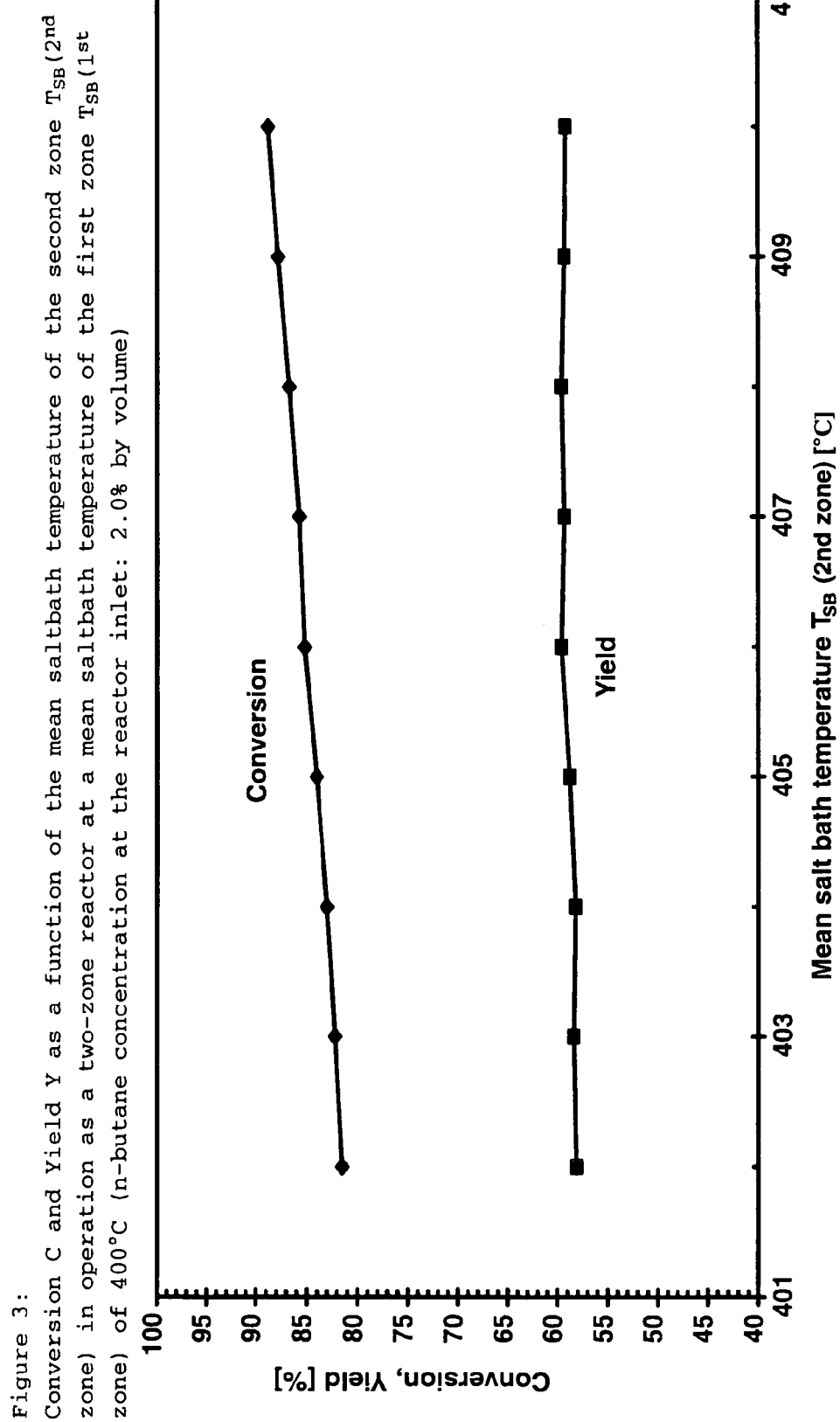

FIG. 3 shows the conversion C and yield Y as a function of the mean salt bath temperature of the second reaction zone $T_{SB}(2^{nd}$ zone). With increasing mean salt bath temperature $T_{SB}(2^{nd}$ zone), the conversion C rises continuously in the range examined, while the yield of maleic anhydride displays a maximum of 59.6% at a mean salt bath temperature $T_{SB, Ymax}(2^{nd}$ zone) of 406–408° C.

Figure 4:
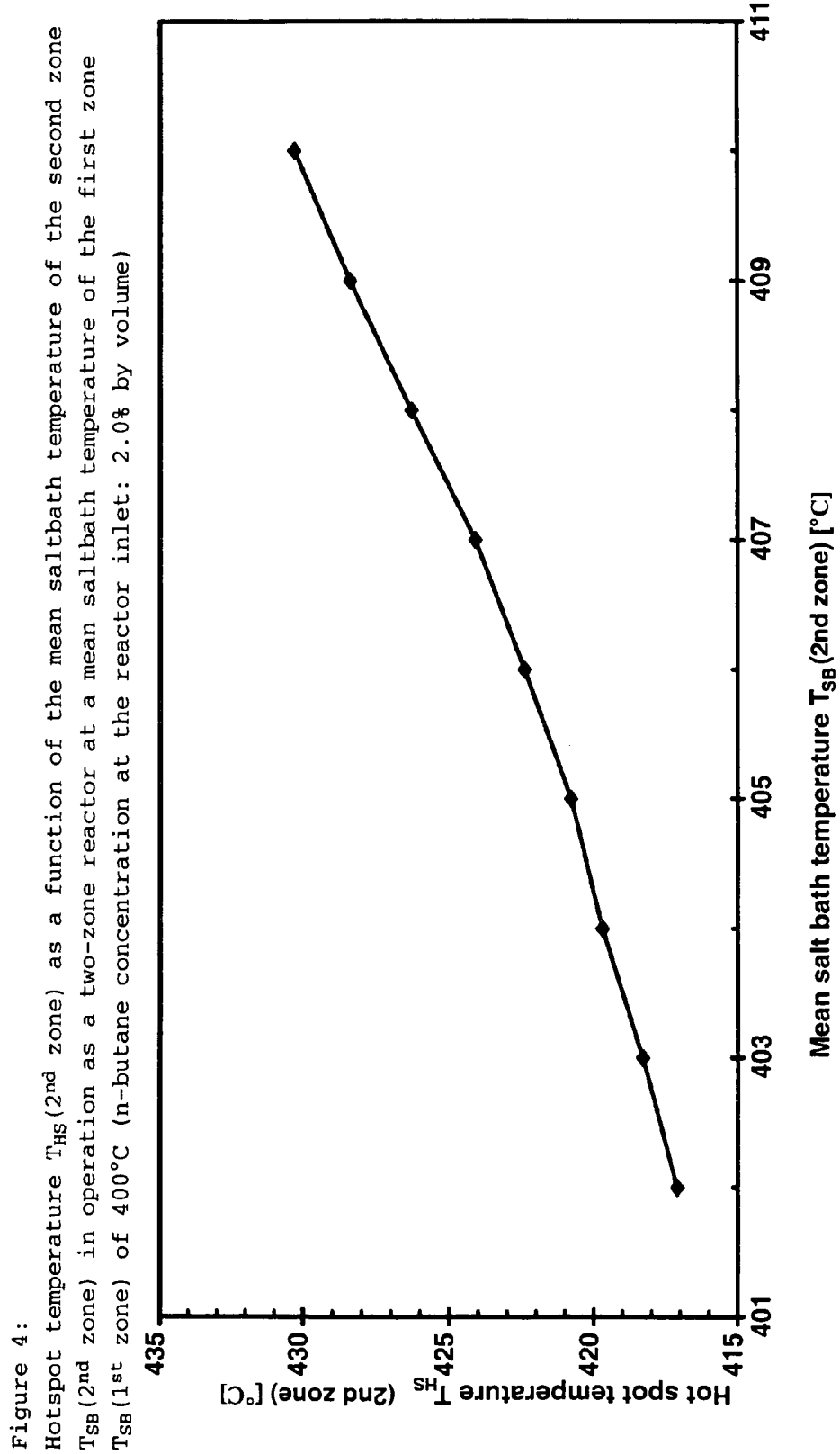

FIG. 4 shows the hotspot temperature of the second reaction zone $T_{HS}(2^{nd}$ zone) as a function of the mean salt bath temperature in the second reaction zone $T_{SB}(2^{nd}$ zone). In the temperature range of $T_{SB}(2^{nd}$ zone) examined, increasing the mean salt bath temperature $T_{SB}(2^{nd}$ zone) by 1° C. resulted in an increase in the hotspot temperature $T^{HS}(2^{nd}$ zone) in the range from 1.1 to 2.2° C. The runaway temperature of the second reaction zone $T_R(2^{nd}$ zone) is thus above 410° C.

Example 2B

Selection of the Operating Range of the Two-zone Reactor

As mentioned under Example 2A, the first reaction zone of the two-zone reactor was operated at a mean salt bath temperature $T_{SB}(1^{st}$ zone) of 400° C.

Since no runaway temperature of the second reaction zone $T_R(2^{nd}$ zone) could be determined in the temperature range of $T_{SB}(2^{nd}$ zone) examined, it can be assumed from Example 2A that this temperature is above 410° C. In accordance with the formula (III), the mean salt bath temperature $T_{SB}(2^{nd}$ zone) is thus, in the interests of safety, to be set to a value of $$T_{SB}(2^{nd}\text{ zone}) \leq 410° \text{ C.} - 1° \text{ C.}$$

Based on the experimentally determined mean salt bath temperature $T_{SB, Ymax}(2^{nd}$ zone) at which the maximum yield of maleic anhydride was achieved in the range $T_{SB}(2^{nd}$ zone)$\leq 410°$ C. of 406–408° C. (mean: 407° C.), formula (IV) gives a range for the mean salt bath temperature $T_{SB}(2^{nd}$ zone) to be set of $$407°\text{ C.}-10°\text{ C.} \leq T_{SB}(2^{nd}\text{ zone}) \leq 407°\text{ C.}+10°\text{ C.}$$

The mean salt bath temperature $T_{SB}(2^{nd}$ zone) for operation of the two-zone reactor in accordance with the present invention when using the chosen catalyst and under the operating conditions selected is thus in the range from 397 to 409° C. However, to obtain the highest possible yield of maleic anhydride and to achieve a very high level of safety, it is particularly advantageous to carry out the process at a mean salt bath temperature $T_{SB}(2^{nd}$ zone) in the range from (407–5)° C. to (410–2)° C., i.e. in the range from 402 to 408° C., which corresponds to a yield of maleic anhydride of from about 58.1 to 59.6%. In particular, to achieve a particularly high level of safety, it is highly advantageous to carry out the process at a mean salt bath temperature $T_{SB}(2^{nd}$ zone) in the range from (407–5)° C. to (410–4)° C., i.e. in the range from 402 to 406° C., which corresponds to a yield of maleic anhydride of from about 58.1 to 59.6%.

A comparison of Examples 1 and 2 shows the particular advantage of a multizone reactor, i.e. in the present case a two-zone reactor. While in the case of the single-zone reactor, very particularly advantageous operation in terms of yield and safety can be achieved at a mean salt bath temperature $T_{SB}(1^{st}$ zone) in the range from 399 to 401.3° C., which makes a yield of maleic anhydride of from about 56.9 to 58.7% possible, under the present conditions, use of a two-zone reactor at a mean salt bath temperature $T_{SB}(1^{st}$ zone) of 400° C. and a mean salt bath temperature $T_{SB}(2^{nd}$ zone) in the range from 402 to 406° C. enables a maleic anhydride yield of from about 58.1 to 59.6% to be achieved with comparably high safety. The yield which can be achieved by use of a two-zone reactor is thus about 2% relative higher than when using a single-zone reactor.

Example 3

Single-zone Reactor (2.2% by Volume of N-butane)

In the case of the single-zone reactor, both heat transfer medium circuits were operated at the same salt bath temperature. The reaction conditions set were as follows:

| | |
|---|---|
| Total amount of catalyst installed: | 2144 ml |
| Concentration of n-butane at the reactor inlet: | 2.2% by volume |
| GHSV: | 2000 standard $l/l_{catalyst} \cdot h$ |
| Concentration of triethyl phosphate (TEP) at the reactor inlet: | 2 ppm by volume |
| Concentration of water vapor at the reactor inlet: | 3% by volume |

Example 3 was carried out subsequent to Example 2 using the catalyst employed there.

Example 3A

Determination of the Runaway Temperature $T_R(1^{st}$ Zone)

The abovementioned reaction conditions and a mean salt bath temperature $T_{SB}$ of 404° C. were set and the establishment of a stable operating state, i.e. a state in which the drift of the hotspot temperature $T_{HS}(1^{st}$ zone) was $\leq 0.5°$ C. over a period of 24 hours, was awaited. The mean salt bath temperature was then increased in steps of 1° C. After a stable operating state had been reached each time, the hotspot temperature $T_{HS}(1^{st}$ zone), the conversion C, the yield Y and the selectivity S were determined in each case. At the salt bath temperatures set, all hotspots were located in the region of the upper heat transfer medium circuit.

Figure 5:
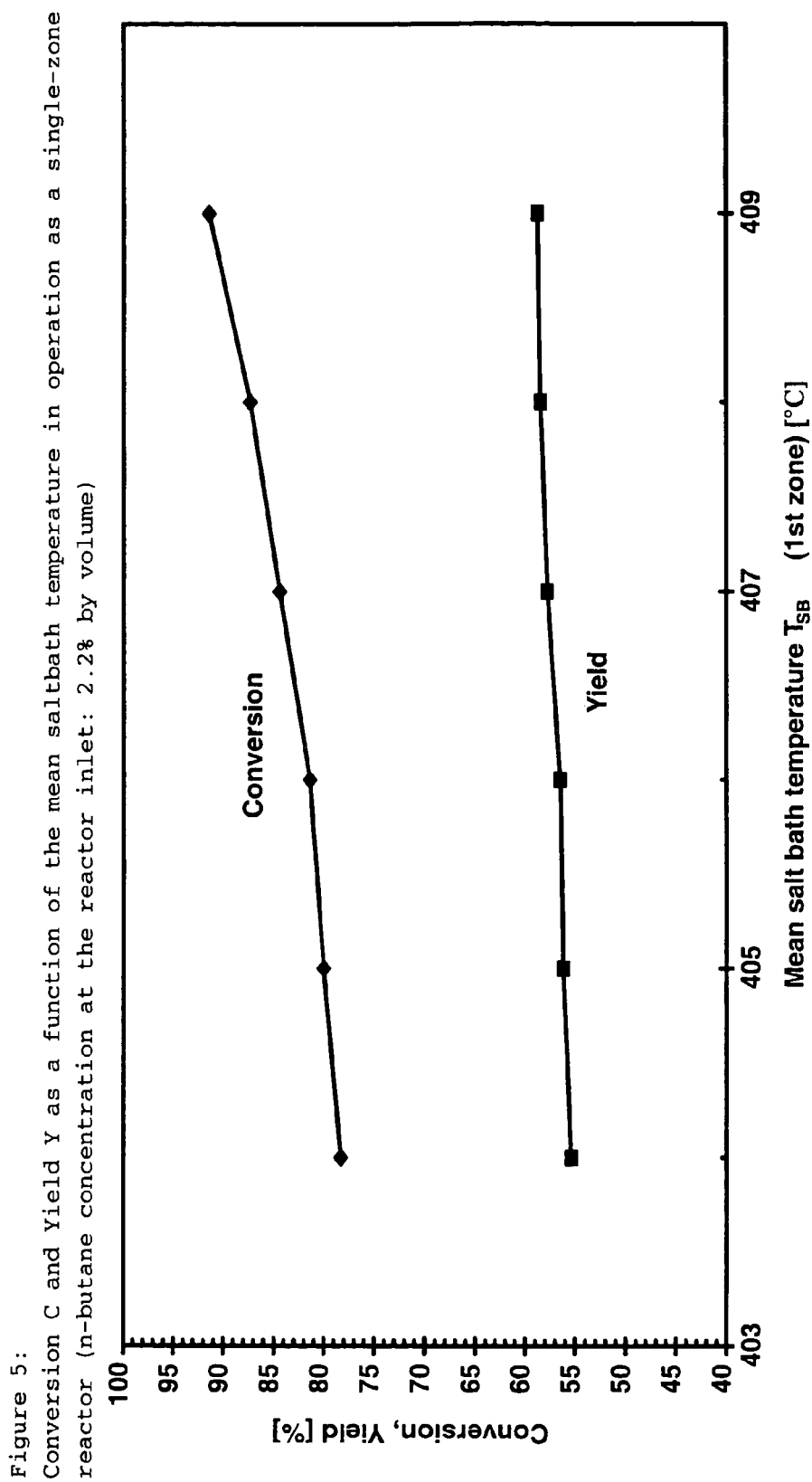

FIG. 5 shows the conversion C and yield Y as a function of the mean salt bath temperature. With increasing mean salt bath temperature, both the conversion C and the yield of maleic anhydride increase continuously in the range examined.

Figure 6:
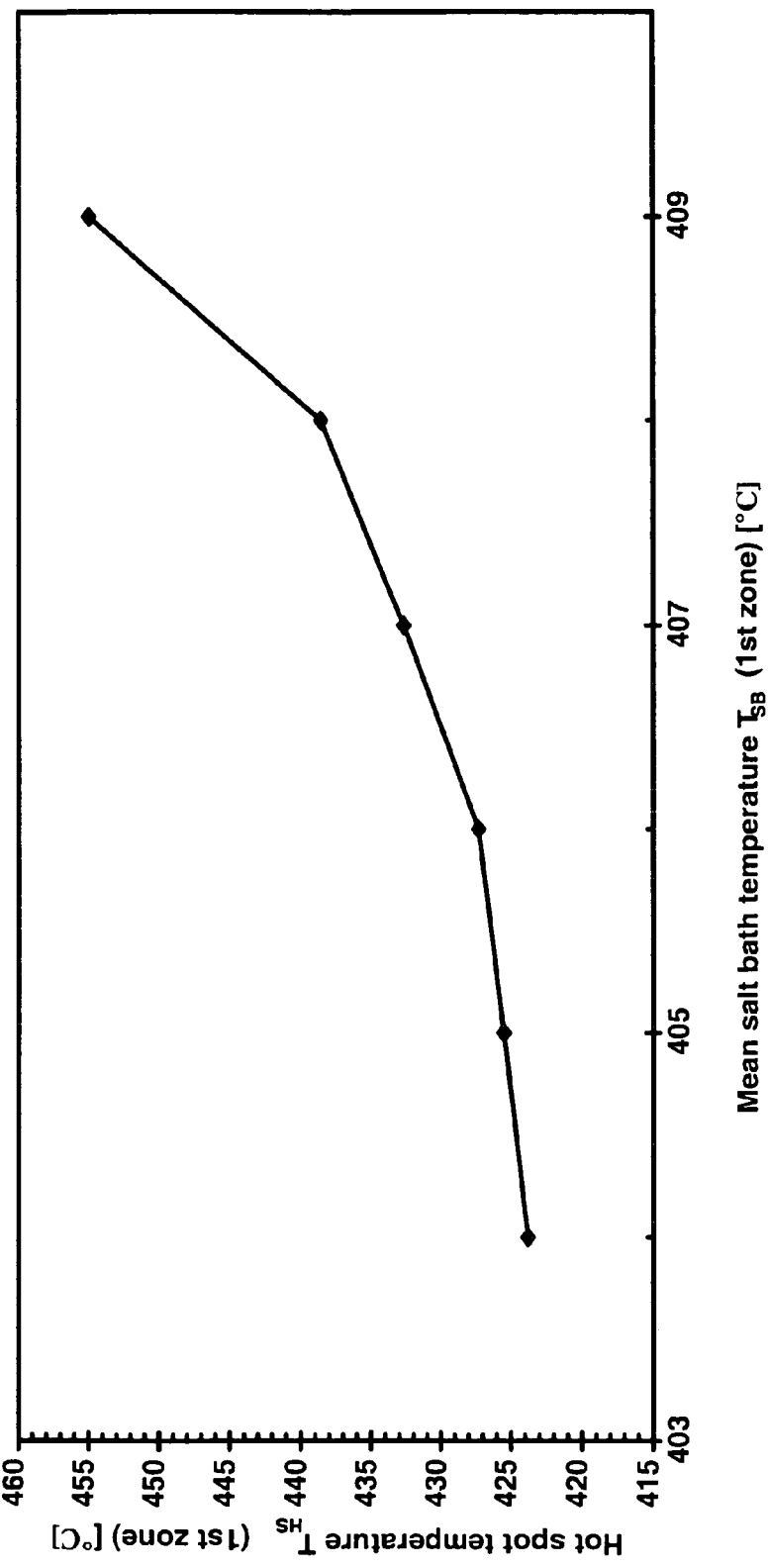

FIG. 6 shows the hotspot temperature $T_{HS}(1^{st}$ zone) as a function of the mean salt bath temperature $T_{SB}(1^{st}$ zone). An increase of 1° C. in the mean salt bath temperature $T_{SB}(1^{st}$ zone) from 405° C. to 406° C. leads to an increase of 1.8° C. in the hotspot temperature $T_{HS}(1^{st}$ zone). A further increase of 1° C. in the mean salt bath temperature $T_{SB}(1^{st}$ zone) to 407° C. leads to an increase of 5.4° C. in the hotspot temperature $T_{HS}(1^{st}$ zone). The runaway temperature $T_R(1^{st}$ zone) is thus between 406 and 407° C. An approximate evaluation on the basis of linear interpolation between the measured values gives a runaway temperature $T_R(1^{st}$ zone) of about 406.9° C.

Example 3B

Selection of the Operating Range for the Single-zone Reactor

On the basis of the experimentally determined runaway temperature $T_R(1^{st}$ zone) of 406.9° C., formula (I) gives a range for the mean salt bath temperature $T_{SB}(1^{st}$ zone) to be set of $$T_{SB}(1^{st}\text{ zone}) \leq 406.9°\text{ C.}-1°\text{ C.}$$

The maximum yield of maleic anhydride in the range $T^{SB}(1^{st}$ zone) $\leq 406.9°$ C. is achieved at 406.9° C. and is about 57.8%. Formula (II) then gives a range for the mean salt bath temperature $T_{SB}(1^{st}$ zone) to be set of $$406.9°\text{ C.}-20°\text{ C.} \leq T_{SB}(1^{st}\text{ zone}) \leq 406.9°\text{ C.}+10°\text{ C.}$$

The mean salt bath temperature $T_{SB}(1^{st}$ zone) for operation of the single-zone reactor in accordance with the present invention when using the chosen catalyst and under the operating conditions selected is thus in the range from 386.9 to 405.9° C. However, to obtain the highest possible yield of maleic anhydride and to achieve a very high level of safety, it is particularly advantageous to carry out the process at a mean salt bath temperature $T_{SB}(1^{st}$ zone) in the range from (406.9–5)° C. to (406.9–2)° C., i.e. in the range from 401.9 to 404.9° C., which corresponds to a yield of maleic anhydride of up to 56.2%.

It may be emphasized that the experimentally determined maximum maleic anhydride yield in the overall range examined of 58.8% is achieved at a mean salt bath temperature $T^{SB}(1^{st}$ zone) of 409° C., which is thus significantly above the runaway temperature $T_R(1^{st}$ zone). If, contrary to the teachings of the present invention, the process were to be operated at this temperature, there would be a risk of sudden, uncontrollable temperature peaks in the catalyst bed of the shell-and-tube reactor which could irreversibly damage the catalyst. Furthermore, there would be a risk of a runaway reaction in individual reaction tubes through to the entire shell-and-tube reactor.

The measures prescribed by the present invention rule out this hazardous range and ensure safe operation of the process and also avoid premature thermal damage to the catalyst.

Example 4

Two-zone Reactor (2.2% by Volume of N-butane)

The reaction conditions set were as follows:

| | |
|---|---|
| Total amount of catalyst installed: | 2144 ml |
| Concentration of n-butane at the reactor inlet: | 2.2% by volume |
| GHSV: | 2000 standard $l/l_{catalyst} \cdot h$ |
| Concentration of triethyl phosphate (TEP) at the reactor inlet: | 2 ppm by volume |
| Concentration of water vapor at the reactor inlet: | 3% by volume |

Since the reaction conditions in the upper reaction zone of the single-zone reactor and the first reaction zone of the two-zone reactor are identical, the runaway temperature $T^R(1^{st}$ zone$)$ of the single-zone reactor is also identical to the runaway temperature of the first reaction zone $T_R(1^{st}$ zone$)$ of the two-zone reactor. The determination of the runaway temperature of the first reaction zone $T_R(1^{st}$ zone$)$ of the two-zone reactor and the selection of the appropriate operating range as in Example 3.

The first reaction zone of the two-zone reactor is thus to be operated at a mean salt bath temperature $T_{SB}(1^{st}$ zone$)$ in the range from 386.9 to 405.9° C. and particularly advantageously in the range from 401.9 to 404.9° C. when using the chosen catalyst and under the operating conditions selected.

Example 4A

Determination of the Runaway Temperature $T_R(2^{nd}$ Zone$)$

In the present example, the first reaction zone of the two-zone reactor was operated at a mean salt bath temperature $T_{SB}(1^{st}$ zone$)$ of 404° C.

The catalyst was operated initially at a mean salt bath temperature of the first reaction zone $T_{SB}(1^{st}$ zone$)$ of 404° C. and a mean salt bath temperature of the second reaction zone $T_{SB}(2^{nd}$ zone$)$ of 411° C. until a stable operating state had been established. The mean salt bath temperature of the second reaction zone $T_{SB}(2^{nd}$ zone$)$ was then increased in steps of 1° C. and the establishment of a stable operating state, i.e. a state in which the drift of the hotspot temperature $T_{HS}(2^{nd}$ zone$)$ was $\leq 0.5°$ C. over a period of 24 hours, was awaited each time. After a stable operating state had been reached, the hotspot temperature $T_{HS}(2^{nd}$ zone$)$, the conversion C, the yield Y and the selectivity S were determined in each case.

Figure 7:
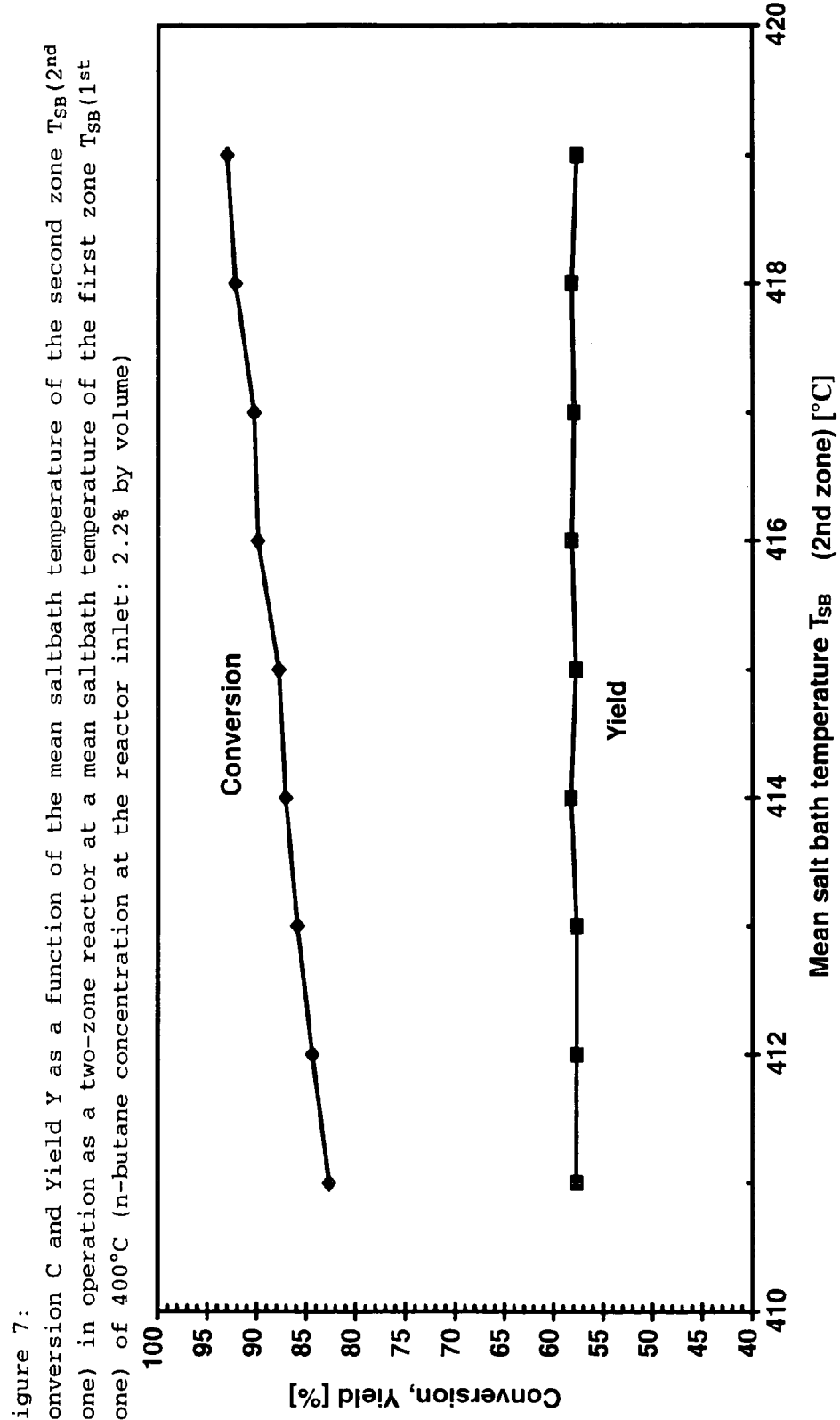

FIG. 7 shows the conversion C and yield Y as a function of the mean salt bath temperature of the second reaction zone $T_{SB}(2^{nd}$ zone$)$. With increasing mean salt bath temperature $T_{SB}(2^{nd}$ zone$)$, the conversion C rises continuously in the range examined, while the yield of maleic anhydride displays a flat maximum of about 58.2% at a mean salt bath temperature $T_{SB, Ymax}(2^{nd}$ zone$)$ of 414–418° C.

Figure 8:
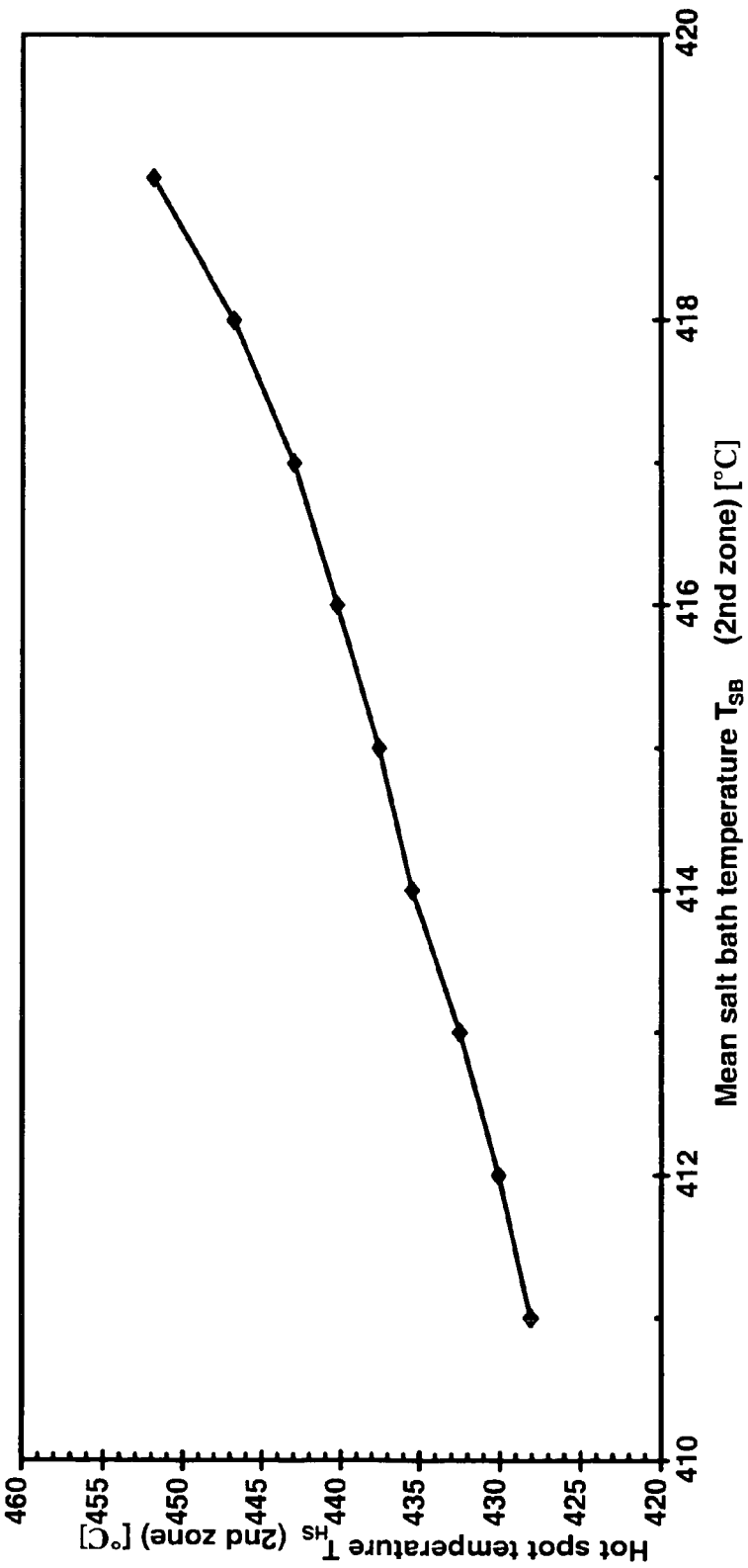

FIG. 8 shows the hotspot temperature $T_{HS}(2^{nd}$ zone$)$ as a function of the mean salt bath temperature $T_{SB}(2^{nd}$ zone$)$. An increase of 1° C. in the mean salt bath temperature $T_{SB}(2^{nd}$ zone$)$ from 417° C. to 418° C. leads to an increase of 3.8° C. in the hotspot temperature $T_{HS}(2^{nd}$ zone$)$. A further increase of 1° C. in the mean salt bath temperature $T_{SB}(2^{nd}$ zone$)$ to 419° C. leads to an increase of 5.1° C. in the hotspot temperature $T_{HS}(2^{nd}$ zone$)$. The runaway temperature $T_R(2^{nd}$ zone$)$ is thus between 418 and 419° C. An approximate evaluation on the basis of linear interpolation between the measured values gives a runaway temperature $T_R(2^{nd}$ zone$)$ of about 418.8° C.

Example 4B

Selection of the Operating Range of the Two-zone Reactor

As mentioned under Example 4A, the first reaction zone of the two-zone reactor was operated at a mean salt bath temperature $T_{SB}(1^{st}$ zone$)$ of 404° C.

Based on the experimentally determined runaway temperature $T_R(2^{nd}$ zone$)$ of 418.8° C., formula (III) gives a range for the mean salt bath temperature $T_{SB}(2^{nd}$ zone$)$ to be set of $$T_{SB}(2^{nd}\ zone) \leq 418.8°\ C. -1°\ C.$$

Based on the experimentally determined mean salt bath temperature $T_{SB, Ymax}(2^{nd}$ zone$)$ at which the maximum yield of maleic anhydride was achieved in the range $T_{SB}(2^{nd}$ zone$) \leq 418.8°$ C. of 414–418° C. (mean: 416° C.), formula (IV) gives a range for the mean salt bath temperature $T_{SB}(2^{nd}$ zone$)$ to be set of $$416°\ C. -10°\ C. \leq T_{SB}(2^{nd}\ zone) \leq 416°\ C. +10°\ C.$$

The mean salt bath temperature $T_{SB}(2^{nd}$ zone$)$ for operation of the two-zone reactor in accordance with the present invention when using the chosen catalyst and under the operating conditions selected is thus in the range from 406 to 417.8° C. However, to obtain the highest possible yield of maleic anhydride and to achieve a very high level of safety, it is particularly advantageous to carry out the process at a mean salt bath temperature $T_{SB}(2^{nd}$ zone$)$ in the range from $(416-5)°$ C. to $(418.8-2)°$ C., i.e. in the range from 411 to 416.8° C., which corresponds to a yield of maleic anhydride of from about 57.7 to 58.2%.

A comparison of Examples 3 and 4 also shows the particular advantage of a multizone reactor, i.e. in the present case a two-zone reactor. While in the case of the single-zone reactor, very particularly advantageous operation in terms of yield and safety can be achieved at a mean salt bath temperature $T_{SB}(1^{st}$ zone$)$ in the range from 401.9 to 404.9° C., which makes a yield of maleic anhydride of up to 56.2% possible, under the present conditions, use of a two-zone reactor at a mean salt bath temperature $T_{SB}(1^{st}$ zone$)$ of 404° C. and a mean salt bath temperature $T_{SB}(2^{nd}$ zone$)$ in the range from 411 to 416.8° C. enables a maleic anhydride yield of from about 57.7 to 58.2% to be achieved with comparably high safety.

TABLE 2

Experimental data for determining the runaway temperature
$T_R$(1st zone) in operation as a single-zone reactor (Example 1)
and the runaway temperature of the first reaction zone
$T_R$(1st zone) in operation as a two-zone reactor (Example 2)

| $T_{SB}$ (1st zone) [° C.] | $T_{HS}$ (1st zone) [° C.] | $\Delta T_{HS}$(1st zone) when $T_{SB}$(1st zone) is increased by 1° C. [° C.] | Yield Y [%] | Selectivity S [%] | Conversion C [%] |
|---|---|---|---|---|---|
| 393 | 407.2 | 2.1 (interpolated) | 51.5 | 74.0 | 69.6 |
| 395 | 411.3 | 1.4 (interpolated) | 54.0 | 72.8 | 74.2 |
| 397 | 414.0 | 1.9 (interpolated) | 55.2 | 72.5 | 76.2 |
| 399 | 417.7 | 2.3 (interpolated) | 56.9 | 71.7 | 79.4 |
| 401 | 422.3 | 1.4 | 58.7 | 70.2 | 83.7 |
| 402 | 423.7 | 1.8 | 59.6 | 69.8 | 85.4 |
| 403 | 425.5 | 3.2 | 59.8 | 68.9 | 86.8 |
| 404 | 428.7 | 3.3 | 61.1 | 67.2 | 91.0 |
| 405 | 432.0 | 10.0 | 60.9 | 65.9 | 92.6 |
| 406 | 442.0 | — | 60.7 | 64.2 | 94.6 |

During the entire trial, the following parameters were kept constant:

| | |
|---|---|
| concentration of n-butane at the reactor inlet = | 2.0% by volume |
| GHSV = | 2000 standard l/l$_{catalyst}$ · h |
| pressure at the reactor outlet = | 0.2 MPa abs |
| concentration of triethyl phosphate (TEP) = | 2 ppm by volume |
| concentration of water vapor = | 3% by volume |

TABLE 3

Experimental data for determining the runaway temperature
of the second reaction zone $T_R$(2nd zone) at a mean saltbath
temperature of the first zone $T_{SB}$(1st zone) of 400° C.
in operation as two-zone reactor (Example 2)

| $T_{SB}$ (2nd zone) [° C.] | $T_{HS}$ (2nd zone) [° C.] | $\Delta T_{HS}$(2nd zone) when $T_{SB}$(2nd zone) is increased by 1° C. [° C.] | Yield Y [%] | Selectivity S [%] | Conversion C [%] |
|---|---|---|---|---|---|
| 402 | 417.1 | 1.2 | 58.1 | 71.3 | 81.5 |
| 403 | 418.3 | 1.4 | 58.4 | 71.0 | 82.2 |
| 404 | 419.7 | 1.1 | 58.2 | 70.1 | 83.0 |
| 405 | 420.8 | 1.6 | 58.8 | 70.0 | 84.0 |
| 406 | 422.4 | 1.7 | 59.6 | 70.0 | 85.2 |
| 407 | 424.1 | 2.2 | 59.3 | 69.2 | 85.7 |
| 408 | 426.3 | 2.1 | 59.6 | 68.7 | 86.7 |
| 409 | 428.4 | 1.9 | 59.3 | 67.5 | 87.8 |
| 410 | 430.3 | — | 59.2 | 66.7 | 88.8 |

During the entire trial, the following parameters were kept constant:

| | |
|---|---|
| concentration of n-butane at the reactor inlet = | 2.0% by volume |
| GHSV = | 2000 standard l/l$_{catalyst}$ · h |
| pressure at the reactor outlet = | 0.2 MPa abs |
| concentration of triethyl phosphate (TEP) = | 2 ppm by volume |
| concentration of water vapor = | 3% by volume |

TABLE 4

Experimental data for determining the runaway temperature
$T_R$(2nd zone) in operation as a single-zone reactor (Example 3)
and the runaway temperature of the first reaction zone
$T_R$(1st zone) in operation as a two-zone reactor (Example 4)

| $T_{SB}$ (1st zone) [° C.] | $T_{HS}$ (1st zone) [° C.] | $\Delta T_{HS}$(1st zone) when $T_{SB}$(1st zone) is increased by 1° C. [° C.] | Yield Y [%] | Selectivity S [%] | Conversion C [%] |
|---|---|---|---|---|---|
| 404 | 423.8 | 1.7 | 55.4 | 70.8 | 78.3 |
| 405 | 425.5 | 1.8 | 56.2 | 70.3 | 80.0 |
| 406 | 427.3 | 5.4 | 56.5 | 69.4 | 81.4 |
| 407 | 432.7 | 5.9 | 57.8 | 68.5 | 84.4 |
| 408 | 438.6 | 16.4 | 58.5 | 67.0 | 87.3 |
| 409 | 455.0 | — | 58.8 | 64.3 | 91.4 |

During the entire trial, the following parameters were kept constant:

| | |
|---|---|
| concentration of n-butane at the reactor inlet = | 2.2% by volume |
| GHSV = | 2000 standard l/l$_{catalyst}$ · h |
| pressure at the reactor outlet = | 0.2 MPa abs |
| concentration of triethyl phosphate (TEP) = | 2 ppm by volume |
| concentration of water vapor = | 3% by volume |

TABLE 5

Experimental data for determining the runaway temperature
of the second reaction zone $T_R$(2nd zone) at a mean saltbath
temperature of the first zone $T_{SB}$(1st zone) of 404° C.
in operation as two-zone reactor (Example 4)

| $T_{SB}$ (2nd zone) [° C.] | $T_{HS}$ (2nd zone) [° C.] | $\Delta T_{HS}$(2nd zone) when $T_{SB}$(2nd zone) is increased by 1° C. [° C.] | Yield Y [%] | Selectivity S [%] | Conversion U [%] |
|---|---|---|---|---|---|
| 411 | 428.1 | 2.0 | 57.7 | 69.8 | 82.7 |
| 412 | 430.1 | 2.4 | 57.7 | 68.4 | 84.4 |
| 413 | 432.5 | 3.0 | 57.7 | 67.2 | 85.9 |
| 414 | 435.5 | 2.1 | 58.3 | 66.9 | 87.1 |
| 415 | 437.6 | 2.7 | 57.8 | 65.8 | 87.8 |
| 416 | 440.3 | 2.7 | 58.2 | 64.7 | 89.9 |

TABLE 5-continued

Experimental data for determining the runaway temperature of the second reaction zone $T_R(2^{nd}\text{ zone})$ at a mean saltbath temperature of the first zone $T_{SB}(1^{st}\text{ zone})$ of 404° C. in operation as two-zone reactor (Example 4)

| $T_{SB}$ (2$^{nd}$ zone) [° C.] | $T_{HS}$ (2$^{nd}$ zone) [° C.] | $\Delta T_{HS}(2^{nd}\text{ zone})$ when $T_{SB}(2^{nd}\text{ zone})$ is increased by 1° C. [° C.] | Yield Y [%] | Selectivity S [%] | Conversion U [%] |
|---|---|---|---|---|---|
| 417 | 443.0 | 3.8 | 58.0 | 64.2 | 90.3 |
| 418 | 446.8 | 5.1 | 58.2 | 63.1 | 92.2 |
| 419 | 451.9 | — | 57.7 | 62.0 | 93.0 |

During the entire trial, the following parameters were kept constant:

| | |
|---|---|
| concentration of n-butane at the reactor inlet = | 2.2% by volume |
| GHSV = | 2000 standard l/l$_{catalyst}$·h |
| pressure at the reactor outlet = | 0.2 MPa abs |
| concentration of triethyl phosphate (TEP) = | 2 ppm by volume |
| concentration of water vapor = | 3% by volume |

We claim:

1. A process for preparing maleic anhydride comprising heterogeneously catalyzed gas-phase oxidation of hydrocarbons having at least four carbon atoms by means of oxygen-containing gases at from 350 to 500° C. in the presence of a volatile phosphorus compound over a vanadium-, phosphorus- and oxygen-containing catalyst in a shell-and-tube reactor unit having at least one reaction zone cooled by means of a heat transfer medium, wherein at least one of the (i) temperature and (ii) the amount of the heat transfer medium flowing into the first (relative to the feed direction) reaction zone is set so that the mean temperature of the heat transfer medium in the first reaction zone $T_{SB}(1^{st}\text{ zone})$, which is calculated as the mean of the inflow temperature and the outflow temperature of the heat transfer medium, is in accordance with the formulae (I) and (II)

$$T_{SB}(1^{st}\text{ zone}) \leq T_R(1^{st}\text{ zone}) - T_{Safety}(1^{st}\text{ zone}) \quad (I)$$

$$T_{SB,\,Ymax}(1^{st}\text{ zone}) - T_A(1^{st}\text{ zone}) \leq T_{SB}(1^{st}\text{ zone}) \leq T_{SB,\,Ymax}(1^{st}\text{ zone}) + T_B(1^{st}\text{ zone}) \quad (II),$$

wherein $T_R(1^{st}\text{ zone})$ is the runaway temperature of the first reaction zone, which corresponds to the mean temperature of the heat transfer medium $T_{SB}(1^{st}\text{ zone})$ at which an increase of 1° C. from a 1° C.-lower mean temperature of the heat transfer medium $T_{SB}(1^{st}\text{ zone})-1°$ C. to $T_{SB}(1^{st}\text{ zone})$ causes an increase of 5° C. in the hotspot temperature in the first reaction zone $T_{HS}(1^{st}\text{ zone})$;

$T_{Safety}(1^{st}\text{ zone})$ is the safety temperature of the first reaction zone and has a value of 1° C.;

$T_{SB,\,Ymax}(1^{st}\text{ zone})$ is the mean temperature of the heat transfer medium in the first reaction zone at which the maximum maleic anhydride yield is achieved in the range $T_{SB}(1^{st}\text{ zone}) \leq T_R(1^{st}\text{ zone})$;

$T_A(1^{st}\text{ zone})$ is 20° C.; and $T_B(1^{st}\text{ zone})$ is 10° C.

2. A process according to claim 1, wherein $T_{Safety}(1^{st}\text{ zone})$ in the formula (II) is 2° C.

3. A process according to claim 1, wherein a shell-and-tube reactor unit having at least two reaction zones cooled by means of a heat transfer medium is used.

4. A process according to claim 3, wherein at least one of the (i) temperature and (ii) the amount of the heat transfer medium flowing into the second (relative to the feed direction) reaction zone is set so that the mean temperature of the heat transfer medium in the second reaction zone $T_{SB}(2^{nd}\text{ zone})$, which is calculated as the mean of the inflow temperature and the outflow temperature of the heat transfer medium, is in accordance with the formulae (III) and (IV)

$$T_{SB}(2^{nd}\text{ zone}) \leq T_R(2^{nd}\text{ zone}) - T_{Safety}(2^{nd}\text{ zone}) \quad (III)$$

$$T_{SB,\,Ymax}(2^{nd}\text{ zone}) - T_A(2^{nd}\text{ zone}) \leq T_{SB}(2^{nd}\text{ zone}) \leq T_{SB,\,Ymax}(2^{nd}\text{ zone}) + T_B(2^{nd}\text{ zone}) \quad (IV),$$

wherein $T_R(2nd\text{ zone})$ is the runaway temperature of the second reaction zone, which corresponds to the mean temperature of the heat transfer medium $T_{SB}(2nd\text{ zone})$ at which an increase of 1° C. from a 1° C.-lower mean temperature of the heat transfer medium $T_{SB}(2^{nd}\text{ zone})-1°$ C. to $T_{SB}(2^{nd}\text{ zone})$ causes an increase of 5° C. in the hotspot temperature in the second reaction zone $T_{HS}(2^{nd}\text{ zone})$;

$T_{Safety}(2^{nd}\text{ zone})$ is the safety temperature of the second reaction zone and has a value of 1° C.;

$T_{SB,\,Ymax}(2^{nd}\text{ zone})$ is the mean temperature of the heat transfer medium in the second reaction zone at which the maximum maleic anhydride yield is achieved in the range $T_{SB}(2^{nd}\text{ zone}) \leq T_R(2^{nd}\text{ zone})$;

$T_A(2^{nd}\text{ zone})$ is 10° C.; and $T_B(2^{nd}\text{ zone})$ is 10° C.

5. A process according to claim 4, wherein $T_{Safety}(2^{nd}\text{ zone})$ in the formula (IV) is 2° C.

6. A process according to claim 3, wherein at least one of the (i) temperature and (ii) the amount of the heat transfer medium flowing into the second reaction zone is set so that the hotspot temperature of the second reaction zone $T_{HS}(2^{nd}\text{ zone})$ is higher than the hotspot temperature of the first reaction zone $T_{HS}(1^{st}\text{ zone})$.

7. A process according to claim 1, wherein a catalyst bed which is structured in respect of its activity is used in at least one of the reaction zones.

8. A process according to claim 1, wherein the hydrocarbon used is n-butane.

9. A process according to claim 1, wherein the volatile phosphorus compound used is a tri($C_1$–$C_4$-alkyl) phosphate.

10. A process according to claim 1, wherein the heterogeneously catalyzed gas-phase oxidation is carried out at a pressure of from 0.1 to 1 MPa abs.

11. A process according to claim 2, wherein a shell-and-tube reactor unit having at least two reaction zones cooled by means of a heat transfer medium is used.

12. A process according to claim 4, wherein at least one of the (i) temperature and (ii) the amount of the heat transfer medium flowing into the second reaction zone is set so that the hotspot temperature of the second reaction zone $T_{HS}(2^{nd}\text{ zone})$ is higher than the hotspot temperature of the first reaction zone $T_{HS}(1^{st}\text{ zone})$.

13. A process according to claim 5, wherein at least one of the (i) temperature and (ii) the amount of the heat transfer medium flowing into the second reaction zone is set so that the hotspot temperature of the second reaction zone $T_{HS}(2^{nd}\text{ zone})$ is higher than the hotspot temperature of the first reaction zone $T_{HS}(1^{st}\text{ zone})$.

14. A process according to claim 2, wherein a catalyst bed which is structured in respect of its activity is used in at least one of the reaction zones.

15. A process according to claim 3, wherein a catalyst bed which is structured in respect of its activity is used in at least one of the reaction zones.

16. A process according to claim 4, wherein a catalyst bed which is structured in respect of its activity is used in at least one of the reaction zones.

17. A process according to claim 2, wherein the hydrocarbon used is n-butane.

18. A process according to claim 4, wherein the hydrocarbon used is n-butane.

19. A process according to claim 4, wherein the volatile phosphorus compound used is a tri($C_1$–$C_4$-alkyl) phosphate.

20. A process according to claim 4, wherein the heterogeneously catalyzed gas-phase oxidation is carried out at a pressure of from 0.1 to 1 MPa abs.

* * * * *